United States Patent
Matsunaga et al.

(10) Patent No.: US 12,054,746 B2
(45) Date of Patent: Aug. 6, 2024

(54) METHOD FOR INDUCING DIFFERENTIATION OF PLURIPOTENT STEM CELLS INTO INTESTINAL EPITHELIAL CELLS

(71) Applicants: PUBLIC UNIVERSITY CORPORATION NAGOYA CITY UNIVERSITY, Nagoya (JP); FUJIFILM Corporation, Tokyo (JP)

(72) Inventors: Tamihide Matsunaga, Nagoya (JP); Takahiro Iwao, Nagoya (JP); Tomoki Kabeya, Nagoya (JP); Shinji Mima, Kanagawa (JP); Toshihide Miyashita, Kanagawa (JP)

(73) Assignees: PUBLIC UNIVERSITY CORPORATION NAGOYA CITY UNIVERSITY, Nagoya (JP); FUJIFILM Corporation, Tokyo (JP)

( * ) Notice: Subject to any disclaimer, the term of this patent is extended or adjusted under 35 U.S.C. 154(b) by 774 days.

(21) Appl. No.: 16/988,145

(22) Filed: Aug. 7, 2020

(65) Prior Publication Data

US 2020/0370020 A1 Nov. 26, 2020

Related U.S. Application Data

(63) Continuation of application No. PCT/JP2019/004553, filed on Feb. 8, 2019.

(30) Foreign Application Priority Data

Feb. 9, 2018 (JP) .................................. 2018-021545

(51) Int. Cl.
C12N 5/071 (2010.01)

(52) U.S. Cl.
CPC ........ *C12N 5/0679* (2013.01); *C12N 2501/11* (2013.01); *C12N 2501/115* (2013.01); *C12N 2501/999* (2013.01); *C12N 2506/45* (2013.01)

(58) Field of Classification Search
CPC .............. C12N 5/0679; C12N 2501/11; C12N 2501/115; C12N 2501/999; C12N 2506/45
See application file for complete search history.

(56) References Cited

U.S. PATENT DOCUMENTS

| | | |
|---|---|---|
| 2012/0028351 A1 | 2/2012 | Li et al. |
| 2017/0349884 A1 | 12/2017 | Karp et al. |
| 2019/0079076 A1 | 3/2019 | Iwao et al. |

FOREIGN PATENT DOCUMENTS

| | | |
|---|---|---|
| JP | 2008-206510 A | 9/2008 |
| JP | 2012-511935 A | 5/2012 |
| WO | 2014/132933 A1 | 9/2014 |
| WO | WO-2014132933 A1 * | 9/2014 ........... C12N 5/0679 |
| WO | 2017/154795 A1 | 9/2017 |

OTHER PUBLICATIONS

Fritz et al. cAMP and EPAC Signaling Functionally Replace OCT4 During Induced Pluripotent Stem Cell Reprogramming. Molecular Therapy. 2015; 23(5): 952-963. (Year: 2015).*
Office Action dated May 4, 2022 issued by the Korean Patent Office in Korean Application No. 10-2020-7022847.
Office Action dated Feb. 4, 2022 from the European Patent Office in EP Application No. 19751317.9.
Extended European Search Report dated Mar. 10, 2021, issued by the European Patent Office in European application No. 19751317.9.
Tomoki Kabeya et al., "Pharmacokinetic functions of human induced pluripotent stem cell-derived small intestinal epithelial cells", Drug Metabolism and Pharmacokinetics, 2020, vol. 35, pp. 374-382.
Maite Rocio Arana et al., "Coordinated induction of GST and MRP2 by CAMP in Caco-2 cells: Role of protein kinase A signaling pathway and toxicological relevance", Toxicology and Applied Pharmacology, 2015, vol. 287, pp. 178-190.
Daisuke Sakano et al., "VMAT2 identified as a regulator of late-stage β-cell differentiation", Nature Chemical Biology, Feb. 2014, vol. 10, pp. 141-148 (10 pages).
Office Action dated Aug. 19, 2021 from the Canadian Patent Office in Application No. 3,090,473.
Office Action dated Aug. 31, 2021 from the Japanese Patent Office Application No. 2019-571161.
Communication dated Sep. 27, 2022, issued in Chinese Application No. 201980012236.8.
Communication dated Aug. 10, 2022, issued in Canadian Application No. 3,090,473.
Office Action dated Nov. 4, 2021, issued by the Korean Intellectual Property Office in Korean application No. 10-2020-7022847.
Ueda et al., "Generation of functional gut-like organ from mouse induced pluripotent stem cells", Biochemical and Biophysical Research Communications, 2010, vol. 391, pp. 38-42 (20 pages total).
McCracken et al., "Generating human intestinal tissue from pluripotent stem cells in vitro", Nat Protoc., 2011, vol. 6, No. 12, 1920-1928, 19 pgs. total.
Spence et al., "Directed differentiation of human pluripotent stem cells into intestinal tissue in vitro", Nature, Feb. 3, 2011, vol. 470, No. 7332, 105-109, 13 pgs. total.
Ogaki et al., "Wnt and Notch Signals Guide Embryonic Stem Cell Differentiation into the Intestinal Lineages", Stem Cells, 2013, vol. 31, No. 6, pp. 1086-1096.

(Continued)

*Primary Examiner* — Arthur S Leonard
*Assistant Examiner* — Jianjian Zhu
(74) *Attorney, Agent, or Firm* — Sughrue Mion, PLLC

(57) ABSTRACT

An object of the present invention is to provide a new means capable of easily and efficiently preparing cells showing a function more similar to the function of intestinal epithelial cells of a living body. According to the present invention, pluripotent stem cells are induced to differentiate into intestinal stem cell-like cells by a method for inducing differentiation of pluripotent stem cells into intestinal epithelial cells, the method including a step (1) of differentiating pluripotent stem, cells into intestinal stem cell-like cells and a step (2) of differentiating the intestinal stem cell-like cells obtained in the step (1) into intestinal epithelial cell-like cells by using an MEK1 inhibitor, a DNA methylation inhibitor, a TGFβ receptor inhibitor, EGF, and a cAMP activator in combination.

16 Claims, 14 Drawing Sheets

(56) References Cited

OTHER PUBLICATIONS

Ozawa et al., "Generation of enterocyte-like cells from human induced pluripotent stem cells for drug absorption and metabolism studies in human small intestine", Scientific Reports, Nov. 2015. 12, vol. 5, No. 16479, 22 pgs. total.

Ogaki S. et al., "A cost-effective system for differentiation of intestinal epithelium from human induced pluripotent stem cells", Scientific Reports, Nov. 30, 2015, vol. 5, No. 17297 (22 pages total).

Iwao et al., "Differentiation of Human Induced Pluripotent Stem Cells into Functional Enterocyte-like Cells Using a Simple Method", Drug Metab. Pharmacokinet., 2014, vol. 29, No. 1, pp. 44-51.

Iwao et al., "Generation of Enterocyte-Like Cells with Pharmacokinetic Functions from Human Induced Pluripotent Stem Cells Using Small-Molecule Compounds", Drug Metab Dispos, Apr. 2015, vol. 43, No. 6, pp. 603-610.

Kodama et al., "Inhibition of mitogen-activated protein kinase kinase, DNA methyltransferase, and transforming growth factor-β promotes differentiation of human induced pluripotent stem cells into enterocytes", Drug Metabolism and Pharmacokinetics, 2016, vol. 31, pp. 193-200.

Kodama et al., "Characteristic Analysis of Intestinal Transport in Enterocyte-Like Cells Differentiated from Human Induced Pluripotent Stem Cells", Drug Metab Dispos, Oct. 2016, vol. 44, pp. 1662-1667.

Kabeya et al., "Cyclic AMP Signaling Promotes the Differentiation of Human Induced Pluripotent Stem Cells into Intestinal Epithelial Cells", Drug Metab Dispos, Oct. 2018, vol. 46, pp. 1411-1419.

International Search Report dated Apr. 23, 2019, issued by the International Searching Authority in application No. PCT/JP2019/004553.

Written Opinion dated Apr. 23, 2019, issued by the International Searching Authority in application No. PCT/JP2019/004553.

International Preliminary Report on Patentability dated Aug. 11, 2020, issued by the International Bureau in application No. PCT/JP2019/004553.

Office Action dated Jan. 5, 2022 from the Japanese Patent Office in Japanese Application No. 2019-571161.

Office Action dated Feb. 5, 2023 from the Chinese Patent Office in Application No. 201980012236.8.

Notification of Reasons for Refusal dated Mar. 7, 2023 from the Japanese Patent Office in Application No. 2022-046424.

Zheng Zhitian, "Peptic Ulcer Disease", People's Health Publishing House, Dec. 31, 1998 (3 total pages).

Chen Jie et al., "Gastrointestinal, hepatobiliary and pancreatic diseases in children", China Medical Science and Technology Press, Nov. 30, 2006 (3 total pages).

Office Action dated Nov. 29, 2023 in European Application No. 19751317.9.

\* cited by examiner

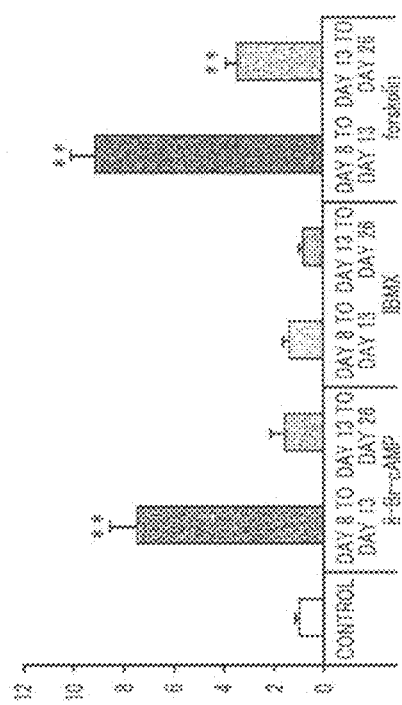
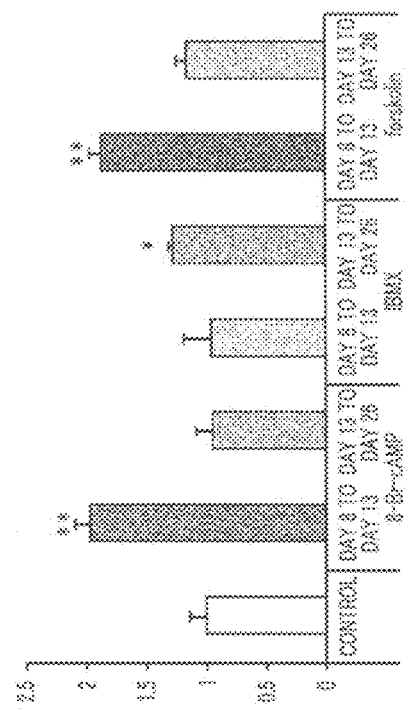
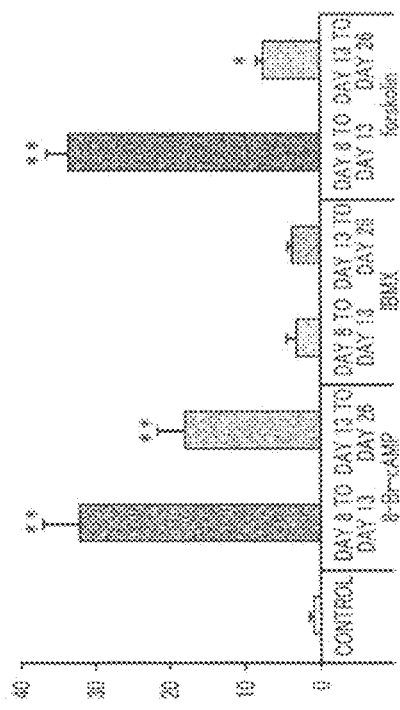
FIG. 2

FIG. 13

| MEDIUM 1 | |
|---|---|
| COMPOSITION | CONCENTRATION |
| RPMI+Glutamax | |
| FBS | 0.5% |
| PENICILLIN/ STREPTOMYCIN | 1% |

| MEDIUM 2 | |
|---|---|
| COMPOSITION | CONCENTRATION |
| RPMI+Glutamax | |
| FBS | 2% |
| PENICILLIN/ STREPTOMYCIN | 1% |

| MEDIUM 3 | |
|---|---|
| COMPOSITION | CONCENTRATION |
| DMEM/F-12 | |
| FBS | 2% |
| PENICILLIN/ STREPTOMYCIN | 1% |
| Glutamax | 1% |

| MEDIUM 4 | |
|---|---|
| COMPOSITION | CONCENTRATION |
| DMEM/F-12 | |
| FBS | 2% |
| PENICILLIN/ STREPTOMYCIN | 1% |
| Glutamax | 1% |
| NON-ESSENTIAL AMINO ACID SOLUTION | 1% |
| B27 supplement | 2% |
| N2 supplement | 1% |

| MEDIUM 5 | |
|---|---|
| COMPOSITION | CONCENTRATION |
| RPMI+Glutamax | 2% |
| FBS | 1% |
| HEPES buffer | 25mM |
| PENICILLIN/ STREPTOMYCIN | 1% |
| NON-ESSENTIAL AMINO ACID SOLUTION | 2% |
| B27 supplement | 1% |
| N2 supplement | 1% |
| HepExtend supplement | |

| MEDIUM 6 | |
|---|---|
| COMPOSITION | CONCENTRATION |
| Advanced DMEM/F-12 | |
| FBS | 2% |
| PENICILLIN/ STREPTOMYCIN | 1% |
| HEPES buffer | 25mM |
| NON-ESSENTIAL AMINO ACID SOLUTION | 1% |
| B27 supplement | 2% |
| N2 supplement | 1% |
| HepExtend supplement | 1% |

METHOD FOR INDUCING DIFFERENTIATION OF PLURIPOTENT STEM CELLS INTO INTESTINAL EPITHELIAL CELLS

CROSS-REFERENCE TO RELATED APPLICATIONS

This application is a Continuation of PCT International Application No. PCT/JP2019/004553 filed on Feb. 8, 2019, which claims priority under 35 U.S.C § 119(a) to Japanese Patent. Application No. 2018-021545 filed on Feb. 9, 2018. Each of the above application(s) is hereby expressly incorporated by reference, in its entirety, into the present application.

BACKGROUND OF THE INVENTION

1. Field of the Invention

The present invention relates to a method for inducing differentiation of pluripotent stem, cells into intestinal epithelial cells and uses of the intestinal epithelial cells.

2. Description of the Related Art

Since many drug metabolizing enzymes and drug transporters are present in small intestine, the small intestine is very important as an organ involved in the first-pass effect of drags, like liver. Therefore, for the development of a drug having excellent pharmacokinetic properties, it is necessary to evaluate the membrane permeability and metabolism of the drug in the small intestine from the early stage of drag development. At present, Caco-2 cells derived from human colon cancer are frequently used as a small intestine model system. However, the expression pattern of a drug transporter in Caco-2 cells is different from that of human small intestine. In addition, it is difficult to accurately evaluate the pharmacokinetics in the small intestine, since Caco-2 cells hardly exhibit the expression and the induction of a drug metabolizing enzyme. Accordingly, it is desirable to use primary intestinal epithelial cells in order to comprehensively evaluate drug metabolism and membrane permeability in the small intestine, but it is difficult to widely use the primary intestinal epithelial cells as a pharmacokinetic test system like primary hepatocytes due to problems in terms of function and supply.

Human induced pluripotent stem (iPS) cells were established in 2007 by Yamanaka et al. The human iPS cells are cells having multiple differentiation potency and almost infinite proliferation ability that are similar to those of human embryonic stem (ES) cells established by Thomson et al. in 1998. The human iPS cells have fewer ethical problems than the human ES cells and are expected to be a stable cell source for drug development.

A method for selectively obtaining intestinal tract stem/progenitor cells from cells derived from the intestinal tract in order to provide intestinal epithelial cells used for drag absorbance tests and the like has been reported (JP2008-206510A). In addition, a method for producing or maintaining pluripotent cells using an ALK5 inhibitor has been proposed (JP2012-511935A).

SUMMARY OF THE INVENTION

Several studies have been reported on the induction of differentiation front iPS cells into intestinal epithelial cells (for example, see Ueda T, et. al., Biochem Biophys Res Common. 2010 Jan. 1; 391 (1): 38-42, McCracken K. W. et. al., Nat Protoc. 2011 Nov. 10; 6 (12): 1920-8, Spence J. R., Nature. 2011 Feb. 3; 470 (7332): 105-109, Ogaki S. et. al, Stem Cells. 2013 June; 31 (6): 1086-1096, Ozawa T. et. al., Sci Rep. 2015 Nov. 12; 5: 16479, and Ogaki S. et. al., Sci Rep. 2015 Nov. 30; 5: 17297), but differentiation induction methods in these studies are complicated, the differentiation efficiency is not sufficient, and pharmacokinetic analysis has not been performed in detail. Furthermore, the differentiation induction methods use a large amount of extremely expensive growth factors and cytokines to induce differentiation and thus is not suitable for practical use. The present inventors have also performed research on differentiation of human iPS cells into intestinal epithelial cells and have reported that the produced intestinal epithelial cell-like cells have various pharmacokinetic functions (WO2014/132933A, Iwao T, et. al., Drug Metab Pharmacokinet, 29 (1), 44-51 (2014), and Iwao T. et. al., Drug Metab Dispos, 43 (6), 603-610 (2015)). In addition, the present inventors have found low-molecular weight compounds and conditions useful for promoting differentiation of human iPS cells into intestinal epithelial cells and acquiring functions (WO2014/132933A, WO2017/154795A, and Iwao T. et. al., Drug Metab Dispos, 43 (6), 603-610 (2015)).

As described above, many researchers have energetically performed studies and have achieved certain results, but there still remains a high need for preparing in vitro functional intestinal epithelial cells that can be used for pharmacokinetic assays, toxicity studies, and the like. In particular, improvements in functional aspects and preparation efficiency are desired. An object of the present invention is to provide a new means capable of easily and efficiently preparing a cell (intestinal epithelial cell-like cell) showing a function more similar to the function of intestinal epithelial cells of a living body.

Under the above problems, the present inventors have conducted detailed investigations with an aim of developing a more efficient differentiation induction method. As a result of the studies, it has been found that, in case of inducing differentiation of intestinal stem cell-like, cells obtained from iPS cells into intestinal epithelial cells, culturing the cells in the presence of a cAMP activator to actively increase an intracellular cAMP level is extremely effective for efficient differentiation induction and maturation (acquisition of function). In addition, useful information on the combination of low-molecular weight compounds used for inducing differentiation and the timing of addition have also been provided.

The intestinal epithelial cell-like cell produced under the culture conditions found as a result of the investigations highly expressed an intestinal epithelial-specific enzyme (drug metabolizing enzyme) and were functionally excellent. The following invention is mainly based on the above results and considerations.

[1] A method for inducing differentiation of pluripotent stem cells into intestinal epithelial cells, the method comprising the following steps (1) and (2):

the step (1) of differentiating pluripotent stem cells into intestinal stem cell-like cells; and the step (2) of differentiating the intestinal stem cell-like cells obtained in the step (1) into intestinal epithelial cell-like cells by using an MEK1 inhibitor, a DNA methylation inhibitor, a TGFβ receptor inhibitor, EGF, and a cAMP activator in combination.

[2] The method according to [1], in which the step (1) consists of the following steps (1-1) and (1-2):

the step (1-1) of differentiating pluripotent stem cells into endoderm-like cells; and the step (1-2) of differentiating the endoderm-like cells obtained in the step (1-1) into intestinal stem cell-like cells.

[3] The method according to [1] or [2], in which a culture period in the step (2) is 7 days to 40 days.

[4] The method according to any one of [1] to [3], in which the step (2) includes any one of the following culture step steps A to D, the culture step A: including a culturing (a-1) in a presence of the EGF and the cAMP activator and a culturing (a-2), which is performed after the culturing (a-1), in a presence of the MEK1 inhibitor, the DNA methylation inhibitor, the TGFβ receptor inhibitor, and the EGF, the culture step B: including a culturing (b-1) in a presence of the EGF and a culturing (b-2), which is performed after the culturing (b-1), in a presence of the MEK1 inhibitor, the DNA methylation inhibitor, the TGFβ receptor inhibitor, the EGF, and the cAMP activator, the culture step C: including a culturing (c-1) in a presence of the EGF and the cAMP activator and a culturing (c-2), which is performed after the culturing (c-1), in a presence of the MEK1 inhibitor, the DNA methylation inhibitor, the TGFβ receptor inhibitor, the EGF, and the cAMP activator, and the culture step D: including a culturing (d-1) in a presence of the MEK1 inhibitor, the DNA methylation inhibitor, the TGFβ receptor inhibitor, the EGF, and the cAMP activator.

[5] The method according to [4], in which a period of the culturing (a-1) is 2 days to 10 days, a period of the culturing (a-2) is 9 days to 29 days, a period of the culturing (b-1) is 2 days to 10 days, a period of the culturing (b-2) is 9 days to 19 days, a period of the culturing (c-1) is 2 days to 10 days, a period of the culturing (c-2) is 9 days to 19 days, and a period of the culturing (d-1) is 15 days to 25 days,

[6] The method according to any one of [1] to [5], in which the cAMP activator is Forskolin.

[7] The method according to any one of [1] to [6], in which the step (2) is performed under a condition in which cAMP is supplied to cells and/or under a condition in which a cAMP-degrading enzyme inhibitor is present.

[8] The method according to [7], in which the condition in which cAMP is supplied to cells is a condition in which 8-Br-cAMP is present in a culture medium.

[9] The method according to [7] or [8], in which the cAMP-degrading enzyme inhibitor is IBMX.

[10] The method according to any one of [4] to [9], in which the culture step B includes a culturing (b-3), which is performed after the culturing (b-2), in a presence of the MEK1 inhibitor, the DNA methylation inhibitor, the TGFβ receptor inhibitor, and the EGF, the culture step C includes a culturing (c-3), which is performed after the culturing (c-2), in a presence of the MEK1 inhibitor, the DNA methylation inhibitor, the TGFβ receptor inhibitor, and the EGF, and the culture step D includes a culturing (d-2), which is performed after the culturing (d-1), in a presence of the MEK1 inhibitor, the DNA methylation inhibitor, the TGFβ receptor inhibitor, and the EGF.

[11] The method according to [10], in which a period of each of the culturing (b-3), the culturing (c-3), and the culturing (d-2) is 1 day to 10 days,

[12] The method according to any one of [1] to [11], in which the MEK1 inhibitor is PD98059, the DNA methylation inhibitor is 5-aza-2'-deoxycytidine, and the TGFβ receptor inhibitor is A-83-01.

[13] The method according to any one of [2] to [12], in which activin A is used as a differentiation-inducing factor in the step (1-1).

[14] The method according to any one of [2] to [13], in which FGF2 or a GSK-3β inhibitor is used as a differentiation-inducing factor in the step (1-2).

[15] The method according to any one of [1] to [14], in which the pluripotent stem cells are induced pluripotent stem cells,

[16] The method according to [15], in which the induced pluripotent stem cells are human induced pluripotent stem cells.

[17] An intestinal epithelial cell-like cell obtained by the method according to any one of [1] to [16].

[18] A method for evaluating pharmacokinetics or toxicity of a test substance using the intestinal epithelial cell-like cell according to [17].

[19] The method according to [18], in which the pharmacokinetics is metabolism, absorbance, excretion, drug interaction, induction of a drug metabolizing enzyme, or induction of a drug transporter.

[20] The method according to [18] or [19], comprising the following steps (i) to (iii):

the step (i) of preparing a cell layer formed of the intestinal epithelial cell-like cell according to [17];

the step (ii) of bringing a test substance into contact with the cell layer; and the step (iii) of quantifying the test substance that has permeated the cell layer and evaluating absorbability or membrane permeability, drug interaction, induction of a drug metabolizing enzyme, induction of a drug transporter, or toxicity of the test substance.

[21] The method according to [18] or [19], comprising the following steps (I) and (II):

the step (I) of bringing the test substance into contact with the intestinal epithelial cell-like cell according to [17]; and the step (II) of measuring and evaluating metabolism or absorbance, drug interaction, induction of a drug metabolizing enzyme, induction of a drug transporter, or toxicity of the test substance.

[22] A cell preparation comprising the intestinal epithelial cell-like cell according to [17].

BRIEF DESCRIPTION OF THE DRAWINGS

FIG. 2. Effect of cAMP activator (Forskolin) on differentiation of human iPS cells into intestinal epithelial cell-like cells (result of experiment 1). The expression amounts of various marker genes were compared. The expression amounts were represented by the average value±S.D. (n=3). * $P<0.05$ vs control group, ** $P<0.01$ vs control group. The control group is a group in which additional components (8-Br-cAMP IBMX. Forskolin) were not added.

FIG. 13. Compositions of culture media used in experiments 1 to 5.

DESCRIPTION OF THE PREFERRED EMBODIMENTS

Figure 1:
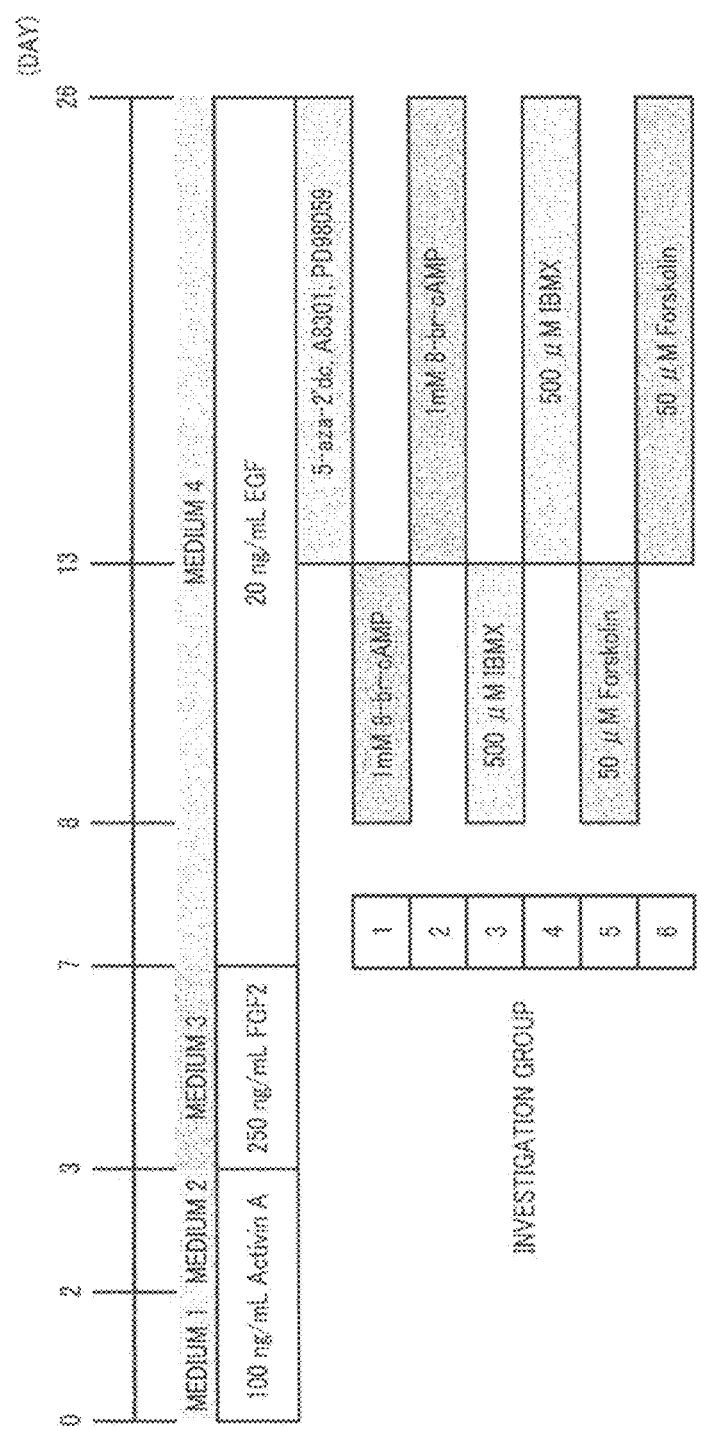
FIG. 1. Protocol of experiment 1 using human iPS cells (Windy). After inducing differentiation into intestinal stem cells by culturing for 3 days (day 0 to day 3) in the presence of activin (Activin A) and for 4 days (day 3 to day 7) in the presence of FGF2, the cells were induced to differentiate into intestinal epithelial cells by culturing for 18 days (day 8 to day 26). The following test groups 1 to 6, in which the components added to the culture medium during inducing differentiation into intestinal epithelial cells were different, were set up, and the effects on differentiation were compared. Test group 1 in which 8-bromo-3',5'-cyclic adenosine monophosphate (8-Br-cAMP) was added to the culture medium in the first half (day 8 to day 13), test group 2 in which 8-Br-cAMP added to the culture medium in the latter half (day 13 to day 26), test group 3 in which 3-isobutyl-1-methylxanthine (IBMX) was added to the culture medium in the first half (day 8 to day 13), test group 4 in which IBMX was added to the culture medium in the latter half (day 13 to day 26), test group 5 in which Forskolin was added to the culture medium in the first half (day 8 to day 13), and test group 6 in which Forskolin was added to the culture medium in the latter half (day 13 to day 26)

The present invention relates to a method for inducing differentiation of pluripotent stem cells into an intestinal epithelial cell lineage (hereinafter, also referred to as "differentiation induction method of the embodiment of the present invention"). According to the present invention, cells that show the characteristics similar to intestinal epithelial cells which constitute the intestinal tissue of a living body, that is, intestinal epithelial cell-like cells are obtained.

"Pluripotent stem cells" refer to cells having the ability (differentiation pluripotency) to differentiate into all cells that constitute a living body and the ability (self-renewal ability) to generate daughter cells having the same differentiation potential as the pluripotent stem cells through cell division. Differentiation pluripotency can be evaluated by transplanting the cells to be evaluated into nude mice and testing for the presence or absence of formation of teratoma including cells of each of the three germ layers (ectoderm, mesoderm, and endoderm).

As the pluripotent stem cells, embryonic stem cells (ES cells), embryonic germ cells (EG cells), induced pluripotent stem cells (iPS cells), and the like can be mentioned, but the pluripotent stem cells are not limited thereto as long as they have differentiation pluripotency and self-renewal ability. The ES cells or the iPS cells are preferably used. The iPS cells are more preferably used. The pluripotent stem cells are preferably mammalian cells (for example, primates such as a human and a chimpanzee, rodents such as a mouse and a rat), and particularly preferably human cells. Accordingly, in the most preferred embodiment of the present invention, human iPS cells are used as the pluripotent stem cells.

The ES cells can be established, for example, by culturing an early embryo before implantation, an inner cell mass constituting the early embryo, a single blastomere, or the like (Manipulating the Mouse Embryo A Laboratory Manual, Second Edition, Cold Spring Harbor Laboratory Press (1994); Thomson, J. A. et. al, Science, 282, 1145-1147 (1998)). As the early embryo, an early embryo produced by nuclear transfer of a somatic cell nucleus may be used (Wilmut et al. (Nature, 385, 810 (1997)), Cibelli et al, (Science, 280, 1256 (1998)), Iriya et al. ((Protein Nucleic Acid Enzyme, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984(1999), Rideout I I I et al. (Nature Genetics, 24, 109 (2000), Tachibana et al. (Human Embryonic Stem Cells Derived by Somatic Cell Nuclear Transfer, Cell (2013) in press)). As an early embryo, a parthenogenetic embryo may be used (Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008)). In addition to the above-mentioned papers, the production of ES cells is described in Strelchenko N., et al. Reprod Biomed Online. 9: 623-629, 2004; Klimanskaya I, et al. Nature 444: 481-485, 2006; Chung Y., et al. Cell Stem Cell 2: 113-117, 2008; Zhang X., et al Stem Cells 24:2669-2676, 2006; Wassarman, R M. et al. Methods in Enzymology, Vol. 365, 2003, or the like. In addition, fused ES cells obtained by cell fusion of ES cells and somatic cells are also included in the embryonic stem cells used in the method of the present invention.

Some ES cells are available from conservation institutions or are commercially available. For example, human ES cells can be available from Kyoto University Research Institute for Regenerative Medicine (for example, KhES-1, KhES-2 and KhES-3), WiCell Research Institute, ESIBIO, or the like.

The EG cells can be established by culturing primordial germ cells in the presence of LIE, bFGF, and SCF (Matsui et al., Cell, 70, 841-847 (1992), Shamblott et al., Proc. Natl. Acad. Sci. USA, 95 (23), 13726-13731 (1998), Turnpenny et al., Stem, Cells, 21 (5), 598-609, (2003)).

"Induced pluripotent stem cells (iPS cells)" are cells that have pluripotency (multiple differentiation potency) and proliferation ability and that are produced by reprogramming somatic cells by introducing reprogramming factors or the like. The induced pluripotent stem cells exhibit properties close to the ES cells. The somatic cells used for producing iPS cells are not particularly limited and may be differentiated somatic cells or undifferentiated stem, cells. In addition, the origin of the somatic cells is not particularly limited but preferably somatic cells of mammals (for example, primates such as a human and a chimpanzee, rodents such as a mouse and a rat) and particularly preferably human somatic cells. The iPS cells can be produced by various methods reported so far. In addition, it is naturally expected that an iPS cell production method to be developed in the future will be applied.

The most basic method for producing iPS cells is a method in which four transcription factors, Oct3/4, Sox2, Klf4, and c-Myc are introduced into cells using a virus (Takahashi K, Yamanaka S: Cell 126 (4), 663-676, 2006; Takahashi, K, et al: Cell 131 (5), 861-72, 2007). It has been reported that human iPS cells have been established by introducing four factors, Oct4, Sox2, Lin28, and Nonog (Yu J, et al: Science 318 (5858), 1917-1920, 2007). It has also been reported that iPS cells have been established by introducing three factors excluding c-Myc (Nakagawa M, et al: Nat. Biotechnol. 26 (1), 101-106, 2008), two factors of Oct3/4 and Klf4 (Kim J B, et al: Nature 454 (7204), 646-650, 2008), or Oct3/4 alone (Kim j B, et al: Cell 136 (3), 411-419, 2009). In addition, a method for introducing a protein, which is an expression product of a gene, into cells (Zhou H, Wu S, Joo J Y, et al: Cell Stem Cell 4, 381-384, 2009; Kim D, Kim C H, Moon J I, et al: Cell Stem Cell 4, 472-476, 2009) has also been reported. On the other hand, it has also been reported that, by using BIX-01294 which is an inhibitor of histone methyltransferase G9a, valproic acid (VPA) which is a histone deacetylase inhibitor, or Bay K8644, production efficiency has been improved and factors to be introduced has been reduced (Huangfu D, et al: Nat. Biotechnol. 26 (7), 795-797, 2008; Huangfu D, et al: Nat. Biotechnol. 26 (11), 1269-1275, 2008; Silva J, et al: PLoS. Biol. 6 (10), e253, 2008). Studies on gene transfer methods have also been performed, and technologies for gene transfer have been developed using, in addition to a retrovirus, a lentivirus (Yu J, et al: Science 318 (5858), 1917-1920, 2007), an adenovirus (Stadtfeld M, et al: Science 322 (5903), 945-949, 2008), a plasmid (Okita K, et al: Science 322 (5903), 949-953, 2008), a transposon vector (Woltjen K, Michael I P, Mohseni P, et al: Nature 458, 766-770, 2009; Kaji K, Norrby K, Paca A, et al: Nature 458, et al. 771-775, 2009; Yusa K, Rad R, Takeda J, et al: Nat Methods 6, 363-369, 2009) or an episomal vector (Yu J, Hu K, Smuga-Otto K, Tian S, et al: Science 324, 797-801, 2009).

Cells transformed to iPS cells, that is, cells that have undergone initialization (reprogramming) can be selected using the expression of pluripotent stem cell markers (undifferentiated markers) such as Fhxo15, Nanog, Oct4, Fgf-4, Esg-1, and Cript, or the like as an index. The selected cells are collected as iPS cells.

The iPS cells can be provided from, for example, National University Corporation Kyoto University, or Independent Administrative Institution RIKEN BioResource Center.

In the present specification, "inducing differentiation" refers to acting to differentiate along a specific cell lineage. In the present invention, iPS cells are induced to differentiate into intestinal epithelial cells. The differentiation induction method of the embodiment of the present invention roughly includes induction steps of two stages, that is, a step (step (1)) of differentiating iPS cells into intestinal stem cell-like cells and a step (step (2)) of differentiating the obtained intestinal stem cell-like cells into intestinal epithelial cell-like cells. Hereinafter, the details of each step will be described.

<Step (1) Differentiation into Intestinal Stem Cell-Like Cells>

In this step, pluripotent stem cells are cultured and differentiated into intestinal stem cell-like cells. In other words, the pluripotent stem cells are cultured under conditions that induce differentiation into intestinal stem cell-like cells. The culture conditions are not particularly limited as long as the pluripotent stem cells differentiate into intestinal stem cell-like cells. Typically, differentiation induction of two stages described below, that is, the differentiation of the pluripotent stem cells into endoderm-like cells (step (1-1)) and the differentiation of endoderm-like cells into intestinal stent cell-like cells (step (1-2)) are performed so that the pluripotent stem cells differentiate into intestinal stem cell-like cells via endoderm-like cells.

Step (1-1) Differentiation into Endoderm-Like Cells

In this step, pluripotent stem cells are cultured and differentiated into endoderm-like cells. In other words, the pluripotent stem cells are cultured under conditions that induce differentiation into endoderm. The culture conditions are not particularly limited as long as the pluripotent stem cells differentiate into endoderm-like cells. For example, the pluripotent stem cells are cultured in a culture medium to which activin A is added, according to a conventional method. In this case, the concentration of activin A in the culture medium, is set to, for example, 10 ng/mL to 200 ng/mL and preferably 20 ng/mL to 150 ng/mL. It is preferable to add serum or a serum substitute (KnockOut™ Serum Replacement (KSR) or the like) to the culture medium from the viewpoints of cell growth rate, maintenance, and the like. The serum is not limited to fetal bovine serum, and human serum, sheep serum, or the like can be also used. The addition amount of serum or a serum substitute is, for example, 0.1% (v/v) to 10% (v/v).

An inhibitor of the Wnt/β-catenin signaling pathway (for example, hexachlorophene, quercetin, or Wnt3a which is a Wnt ligand) may be added to the culture medium to promote differentiation into endoderm-like cells.

One or more of BMP4, VEGF, and FGF2 may be added to the culture medium to promote differentiation into endoderm-like cells. In this case, the concentration of BMP4 in the culture medium is, for example, 0.1 ng/mL to 10 ng/mL and preferably 1 ng/mL to 5 ng/mL, the concentration of VEGF in the culture medium is, for example, 0.5 ng/mL to 100 ng/mL and preferably 1 ng/mL to 20 ng/mL, and the concentration of FGF2 in the culture medium is, for example, 0.2 ng/mL to 50 ng/mL and preferably 0.5 ng/mL to 10 ng/mL.

This step can be also performed with the method described in WO2014/165663A or a method based thereon.

In a preferred aspect, two stage culture is performed as the step (1-1). First stage culture is performed in a culture medium to which a relatively low concentration of serum (for example, 0.1% (v/v) to 1% (v/v)) is added, and subsequent second stage culture is performed in a culture medium having a higher serum concentration than the first stage culturing (for example, a serum concentration of 1% (v/v) to 10% (v/v)). Employing the two stage culture in this manner is preferable since the growth of undifferentiated cells is suppressed by the first stage culture and differentiated cells are proliferated by the subsequent second stage culture.

The period (culture period) of the step (1-1) is, for example, 1 day to 10 days and preferably 2 days to 7 days. In a case where the two stage culture is employed as the step (1-1), the culture period of first stage is, for example, 1 day to 7 days and preferably 2 days to 5 days, and the culture period of second stage is, for example, 1 day to 6 days and preferably 1 day to 4 days.

Step (1-2) Differentiation into Intestinal Stem Cell-Like Cells

In this step, the endoderm-like cells obtained in step (1-1) are cultured and differentiated into intestinal stem cell-like cells. In other words, the endoderm-like cells are cultured under conditions that induce differentiation into intestinal stem, cells-like cells. The culture conditions are not particularly limited as long as the endoderm-like cells differentiate into intestinal stem cell-like cells. The culture is preferably performed in the presence of FGF2 (fibroblast growth factor 2) or in the presence of a GSK-3β inhibitor. Human FGF2 (for example, a human recombinant FGF2) is preferably used as FGF2.

Typically, the cell population or a part thereof obtained through the step (1-1) is used in the step (1-2) without selection. Alternatively, the step (1-2) may be performed after selecting endoderm-like cells from the cell population obtained through step (1-1). The selection of endoderm-like cells may be performed, for example, with a flow cytometer (cell sorter) using a cell surface marker as an index.

"In the presence of FGF2" is synonymous with under the condition in which FGF2 is added to a culture medium. Accordingly, in order to perform culture in the presence of FGF2, a culture medium to which FGF2 is added may be used. The concentration of FGF2 added is, for example, 100 ng/mL to 500 ng/mL.

Similarly, "in the presence of a GSK-3β inhibitor" is synonymous with under the condition in which a GSK-3β inhibitor is added to a culture medium. Accordingly, in order to perform culture in the presence of GSK-3β inhibitor, a culture medium to which FGF2 is added may be used. Examples of the GSK-3β inhibitors include CHIR99021, SB216763, CHIR98014, TWS119, Tideglusib, SB415286, BIO, AZD2858, AZD1080, AR-A014418, TDZD-8, LY2090314, IM-12, Indirubin, Bikinin, 1-Azakenpaullone. The concentration of the GSK-3β inhibitor (in the case of CHIR99021) added is, for example, 1 μM to 100 μM and preferably 3 μM to 30 μM.

The period (culture period) of the step (1-2) is, for example, 2 days to 10 days and preferably 3 days to 7 days. In a case where the culture period is too short, an expected effect (increase in differentiation efficiency or promotion of acquisition of function as intestinal stem cells) cannot be sufficiently obtained. On the other hand, in a case where the culture period is too long, the differentiation efficiency will be reduced.

The differentiation into intestinal stem cell-like cells can be determined or evaluated using, for example, the expression of an intestinal stem cell marker as an index. Examples of the intestinal stem cell markers include G protein-coupled receptor 5 (LGR5) containing leucine-rich repeats and ephrin B2 receptor (EphB2).

<Step (2) Differentiation into Intestinal Epithelial Cell-Like Cells>

In this step, the intestinal stem cell-like cells obtained in the step (1) are differentiated into intestinal epithelial cell-like cells by using an MEK1 inhibitor, a DNA methylation inhibitor, a TGFβ receptor inhibitor, EGF, and a cAMP activator in combination. In the present invention, an intracellular cAMP level is actively increased by using a cAMP activator during the differentiation induction. "Using an MEK1 inhibitor, a DNA methylation inhibitor, a TGFβ receptor inhibitor, EGF, and a cAMP activator in combination" means all these compounds are required in order to perform one or more cultures constituting the step (2), and it is not required, as an essential condition, that all of these compounds are used at the same time, that is, that the culture using a culture medium to which all of these compounds are added is performed.

Typically, the cell population or a part thereof obtained through the step (1) is used in the step (2) without selection. Alternatively, the step (2) may be performed after selecting intestinal stem cell-like cells from the cell population obtained through step (1). The selection of intestinal stem cell-like cells may be performed, for example, with a flow cytometer (cell sorter) using a cell surface marker as an index.

The step (2) is constituted by one or more cultures (details will be described later). In each culture constituting the step (2), a culture medium, for example, a culture medium to which EGF and a cAMP activator are added as essential components, a culture medium in which a MEK1 inhibitor, a DNA methylation inhibitor, a TGFβ receptor inhibitor, and EGF are added as essential components, a culture medium, to which EGF is added as an essential component, a culture medium to which a MEK1 inhibitor, a DNA methylation inhibitor, a TGFβ receptor inhibitor, EGF, and a cAMP activator are added as essential components, or the like is used.

As the MEK1 inhibitors, PD98059, PD184352, PD184161, PD0325901, U0126, MEK inhibitor I, MEK inhibitor II, MEK1/2 inhibitor II, and SL327 can be mentioned. As the DNA methylation inhibitors, 5-aza-2'-deoxycytidine, 5-azacytidine, RG108, and zebularine can be mentioned. Regarding the TGFβ receptor inhibitor, considering that A-83-01 used in Examples described later exhibits an inhibitory activity on TGF-β receptors ALK4, ALK5, and ALK7, it is preferable to use an inhibitor that exhibits an inhibitory activity on one or more of TGF-β receptor, ALK4, ALK5, and ALK7. For example, A-83-01, SB431542, SB-505124, SB525334, D4476, ALK5 inhibitor, LY2157299, LY364947, GW788388, and RepSox satisfy the above condition. As the cAMP activator, Forskolin, indomethacin, NKH477 (colforsin daropate), a cell-derived toxin protein (pertussis toxin, cholera toxin), PACAP-27, PACAP-38, SKF83822, and the like can be used. Forskolin exhibits an adenylate cyclase activating activity and promotes intracellular cAMP synthesis.

The concentration of the MEK1 inhibitor (in the case of PD98059) added is, for example, 4 μM to 100 μM and preferably 10 μM to 40 μM. The concentration of the DNA methylation inhibitor (in the case of 5-aza-2'-deoxycytidine) added is, for example, 1 μM to 25 μM and preferably 2.5 μM to 10 μM, and the concentration of the TGFβ receptor inhibitor (in the case of A-83-01) added is, for example, 0.1 μM to 2.5 μM and preferably 0.2 μM to 1 μM.

The concentration of EGF added is, for example, 5 ng/mL to 100 ng/ml, and preferably 10 ng/mL to 50 ng/mL. In addition, the concentration of the cAMP activator (in the case of Forskolin) added is 1 μM to 200 μM and preferably 5 μM to 100 μM. In addition, in case of using a compound different from the exemplified compounds, that is, PD98059, 5-aza-2'-deoxycytidine, A-83-01, and Forskolin, the addition concentration can be set according to the above-described concentration range by those skilled in the art in consideration of the difference in the properties (especially the difference in activity) between the compound used and the exemplified compounds (PD98059, 5-aza-2'-deoxycytidine, A-83-01, Forskolin). Whether the set concentration range is suitable or not can be confirmed by a preliminary experiment according to Examples described later.

In addition to the conditions described above, the step (2) may be performed under the condition in which cAMP is supplied to cells (referred to as "additional condition 1") and the condition in which a cAMP-degrading enzyme inhibitor is present (referred to as "additional condition 2"), or under any of these conditions. The additional condition 1 (condition in which cAMP is supplied to cells) is synonymous with the condition in which a compound capable of being incorporated into cells and acting as cAMP when taken up into cells is present. Accordingly, in order to satisfy the additional condition 1, for example, a culture medium to which a cAMP derivative that can be incorporated into cells is added may be used. In a case where the additional condition 1 is adopted, it can be expected that the decrease in the intracellular cAMP concentration is suppressed and thus the induction of differentiation into intestinal epithelial cell in particular, the acquisition of a function as intestinal epithelial cells is promoted. That is, the above condition may allow for the preparation of more functional intestinal epithelial cell-like cells. As the cAMP derivatives, PKA activators (for example, 8-Br-cAMP (8-Bromoadenosine-3',5'-cyclic monophosphate sodium salt, CAS Number: 76939-46-3), 6-Bnz-cAMP (N6-Benzoyladenosine-3',5'-cyclic monophosphate sodium salt, CAS Number: 1135306-29-4), cAMPS-Rp ((R)-Adenosine, cyclic 3',5'-(hydrogen phosphorothioate)triethylammonium salt, CAS Number: 151837-09-1), cAMPS-Sp ((S)-Adenosine, cyclic 3',5'-(hydrogen phosphorothioate) triethylammonium salt, CAS Number: 93602-66-5), Dibutyryl-cAMP (N6,O2'-Dibutyryladenosine 3',5'-cyclic monophosphate sodium salt, CAS Number: 16980-89-5), 8-Cl-cAMP (8-Chloroadenosine-3',5'-cyclic monophosphate salt, CAS Number: 124705-03-9)) and Epac activators (Rp-8-Br-cAMPS (8-Bromoadenosine 3',5'-cyclic monophosphothioate, Rp-Isomer sodium salt, CAS Number: 129735-00-8), 8-CPT-cAMP (8-(4-Chlorophenylthio)adenosine 3',5'-cyclic monophosphate, CAS Number: 93882-12-3), 8-pCPT-2'-O-Me-cAMP (8-(4-Chlorophenylthio)-2'-O-methyladenosine 3',5'-cyclic monophosphate monosodium, CAS Number: 634207-53-7), and the like) can be used. The concentration of the cAMP derivative (in the case of 8-Br-cAMP) added is, for example, 0.1 mM to 10 mM, preferably 0.2 mM to 5 mM, and more preferably 0.5 mM to 2 mM. In addition, in case of using a compound different from the exemplified compound, that is, 8-Br-cAMP, the addition concentration can be set according to the above-described concentration range by those skilled in the art in consideration of the difference in the properties (especially the difference in activity) between the compound used and the exemplified compound (8-Br-cAMP). Whether the set concentration range is suitable or not can be confirmed by a preliminary experiment according to Examples described later.

The additional condition 2 (the condition in which a cAMP-degrading enzyme inhibitor is present) is synonymous with the condition in which the cAMP-degrading enzyme inhibitor is added to the culture medium. In a case where the additional condition 2 is adopted, it can be expected that the decrease in the intracellular cAMP concentration is suppressed by the inhibition of cAMP degradation and thus the induction of differentiation into intestinal epithelial cell, in particular, the acquisition of a function as intestinal epithelial cells is promoted. That is, the above condition may allow for the preparation of more functional intestinal epithelial cell-like cells. In addition, in a case where the additional conditions 1 and 2 are used in combination, it is possible to suppress the decrease in intracellular cAMP concentration while supplying cAMP to cells. As a result, the condition becomes effective for maintaining intracellular cAMP at a high level, and it can be expected that efficient induction of differentiation into intestinal epithelial cells is promoted.

The cAMP-degrading enzyme inhibitors include IBMX (3-isobutyl-1-methylxanthine) (MIX), Theophylline, Papaverine, Pentoxifylline (Trental), KS-505, 8-Methoxymethyl-IBMX, Vinpocetine (TCV-3B), EHNA, Trequinsin (HL-725), Lixazinone (RS-82856), (LY-186126), Cilostamide (OPC3689), Bemoradan (RWJ-22867), Anergrelide (BL4162A), Indolidan (LY195115), Cilostazol (OPC-13013), Milrinone (WIN47203), Siguazodan (SKF-94836), 5-Methyl-imazodan (0930), SKF-95654, Pirilobendan (UD-CG115BS), Enoximone (MDL17043), Imazodan (CL914), SKF-94120, Vesnarinone (OPC8212), Rolipram (Ro-20-1724), (ZK-62711), Denbufyll'ine, Zaprinast (M&B-22, 948), Dipyridamole, Zardaverine, AH-21-132, and Sulmazol (AR-L115BS). The concentration of the cAMP-degrading enzyme inhibitor (in the case of IBMX) is, for example, 0.05 mM to 5 mM, preferably 0.1 mM to 3 mM and more preferably 0.2 mM to 1 mM. In addition, in case of using a compound different from the exemplified compound, that is, IBMX, the addition concentration can be set according to the above-described concentration range by those skilled in the art in consideration of the difference in the properties (especially the difference in activity) between the compound used and the exemplified compound (IBMX). Whether the set concentration range is suitable or not can be confirmed by a preliminary experiment according to Examples described later.

The period (culture period) of the step (2) is, for example, 7 days to 40 days and preferably 10 days to 30 days. In a case where the culture period is too short, an expected effect (increase in differentiation efficiency or promotion of acquisition of function as intestinal epithelial cells) cannot be sufficiently obtained. On the other hand, in a case where the culture period is too long, the differentiation efficiency will be reduced.

The differentiation into intestinal epithelial cell-like cells can be determined or evaluated using, for example, the expression of an intestinal epithelial cell marker, the incorporation of a peptide, or the induction of expression of a drag metabolizing enzyme via a vitamin D receptor as an index. Examples of the intestinal epithelial cell markers include ATP-binding cassette transporter B1/multidrug resistance protein 1 (ABCB1/MDR1), ATP-binding cassette transporter G2/breast cancer resistance protein (ABCG2/BCRP), cytochrome P4503A4 (CYP3A4), fatty acid binding protein 2 (FABP2), pregnane X receptor (PXR), solute carrier (SLC) family member 5A1/sodium-coupled glucose transporter 1 (SLC5A1/SGLT1), solute carrier (SLC) family member 15A1/peptide transporter 1 (SLC15A1/PEPT1), solute carrier (SLC) organic anion transporter 2B1 (SLCO2B1/OATP2B1), sucrase-isomaltase, uridine diphosphate-glueuronyl transferase 1A1 (UGT1A1), uridine diphosphate-glueuronyl transferase 1A4 (UGT1A4), Villin 1, and carboxylesterase 2A1 (CES2A1). Among these, sucrase-isomaltase and Villin 1 which are highly specific to the intestinal epithelium, CYP3A4 which is a major drag metabolizing enzyme in the small intestine, SLC15A1/PEPT1 which is involved in peptide absorbance in the small intestine, SLC5A1/SGLT1, a glucose transporter, which is expressed at the apical membrane side of the small intestine, SLCO2B1/OATP2B1 which is involved in the absorbance of organic anions in the small intestine, and CES2A1, a hydrolase, which is highly expressed in the small intestine are particularly effective markers.

To obtain a cell population consisting only of target cells (intestinal epithelial cell-like cells) or a cell population including the target cells in a high proportion (high purity), a cell population after culture may be selected and sorted using a cell surface marker characteristic of the target cells as an index.

As the step (2), any one of the following culture steps A to D is preferably performed.

<Culture Step A>

In culture step A, a culturing (a-1) in the presence of EGF and an intracellular cAMP synthesis stimulator and a culturing (a-2), which is performed after the culturing (a-1), in the presence of a MEK1 inhibitor, a DNA methylation inhibitor, a TGFβ receptor inhibitor, and EGF are performed. In case of performing the two-stage culture in this manner, effects of promoting differentiation into intestinal epithelial cells, maturation, and acquiring functions can be expected. The period of the culturing (a-1) is, for example, 2 days to 10 days and preferably 4 days to 8 days, and the period of the culturing (a-2) is, for example, 9 days to 29 days and preferably 7 days to 27 days. For items not particularly described (compounds usable for each culture, concentration of each compound added, and the like), the corresponding description described above is cited.

The culturing (a-1) may be performed under the condition in which cAMP is supplied to cells (referred to as "additional condition 1") and the condition in which a cAMP-degrading enzyme inhibitor is present (referred to as "additional condition 2"), or under any of these conditions. The same applies to the culturing (a-2). Details of the additional condition 1 and the additional condition 2 are as described above.

<Culture Step B>

In culture step B, a culturing (b-1) in the presence of EGF and a culturing (b-2), which is performed after the culturing (b-1), in the presence of a MEK1 inhibitor, a DNA methylation inhibitor, a TGFβ receptor inhibitor, EGF, and an intracellular cAMP synthesis stimulator are performed. In case of performing the two-stage culture in this manner, effects of promoting differentiation into intestinal epithelial cells, maturation, and acquiring functions can be expected. The period of the culturing (b-1) is, for example, 2 days to 10 days and preferably 4 days to 8 days, and the period of the culturing (b-2) is, for example, 9 days to 19 days and preferably 7 days to 17 days. For items not particularly described (compounds usable for each culture, concentration of each compound added, and the like), the corresponding description described above is cited.

The culturing (b-1) may be performed under the condition in which cAMP is supplied to cells (additional condition 1) and the condition in which a cAMP-degrading enzyme inhibitor is present (additional condition 2), or under any of these conditions. The same applies to the culturing (b-2). Details of the additional condition 1 and the additional condition 2 are as described above.

After the culturing (b-2), culture (culturing (b-3)) in the presence of a MEK1 inhibitor, a DNA methylation inhibitor, a TGFβ receptor inhibitor, and EGF may be performed. The period of this culture is, for example, 1 day to 10 days. In case of performing this culture, effects of promoting differentiation into intestinal epithelial cells, maturation, and acquiring functions can be expected.

<Culture Step C>

In culture step C, a culturing (c-1) in the presence of EGF and an intracellular cAMP synthesis stimulator and a culturing (c-2), which is performed after the culturing (b-1), in the presence of a MEK1 inhibitor, a DNA methylation inhibitor, a TGFβ receptor inhibitor, EGF, and an intracellular cAMP synthesis stimulator are performed. In case of performing the two-stage culture in this manner, effects of promoting differentiation into intestinal epithelial cells, maturation, and acquiring functions can be expected. The period of the culturing (c-1) is, for example, 2 days to 10 days and preferably 4 days to 8 days, and the period of the culturing (c-2) is, for example, 9 days to 19 days and preferably 7 days to 17 days. For items not particularly described (compounds usable for each culture, concentration of each compound added, and the like), the corresponding description described above is cited.

The culturing (c-1) may be performed under the condition in which cAMP is supplied to cells (additional condition 1) and the condition in which a cAMP-degrading enzyme inhibitor is present (additional condition 2), or under any of these conditions. The same applies to the culturing (c-2). Details of the additional condition 1 and the additional condition 2 are as described above.

After the culturing (c-2), culture (culturing (c-3)) in the presence of a MEK1 inhibitor, a DM A methylation inhibitor, a TGFβ receptor inhibitor, and EGF may be performed. The period of this culture is, for example, 1 day to 10 days. In case of performing this culture, effects of promoting differentiation into intestinal epithelial cells, maturation, and acquiring functions can be expected.

<Culture Step D>

In culture step D, a culturing (d-1) in the presence of a MEK1 inhibitor, a DNA methylation inhibitor, a TGFβ receptor inhibitor, EGF, and an intracellular cAMP synthesis stimulator is performed. This culture step is particularly advantageous in that the culture operation is simple, differentiation into intestinal epithelial cells is more effective, and a stable effect can be expected because a compound is used. The period of the culturing (d-1) is, for example, 15 days to 25 days and preferably 17 days to 23 days. For items not particularly described (compounds usable for each culture, concentration of each compound added, and the like), the corresponding description described above is cited.

The culturing (d-1) may be performed under the condition in which cAMP is supplied to cells (additional condition 1) and the condition in which a cAMP-degrading enzyme inhibitor is present (additional condition 2), or under any of these conditions. Details of the additional condition 1 and the additional condition 2 are as described above.

After the culturing (d-1), culture (culturing (d-2)) in the presence of a MEK1 inhibitor, a DNA methylation inhibitor, a TGFβ receptor inhibitor, and EGF may be performed. The period of this culture is, for example, 1 day to 10 days. In case of performing this culture, effects of promoting differentiation into intestinal epithelial cells, maturation, and acquiring functions can be expected.

In each of the steps ((1), (1-1), (1-2), (2), (a-1), (a-2), (b-1), (b-2), (b-3), (c-1), (c-2), (c-3), (d-1), and (d-2)), which are capable of constituting the present invention, subculture may be performed in the middle of each of the steps. For example, in a case where cells become confluent or subconfluent a part of the cells are collected and transferred to another culture vessel, and the culture is continued. It is preferable to set a cell density low in order to promote differentiation. For example, cells may be seeded at a cell density of about $1 \times 10^4$ cells/cm$^2$ to $1 \times 10^6$ cells/cm$^2$.

In case of recovering cells due to medium exchange or subculture, cells may be treated in advance with a ROCK inhibitor (Rho-associated coiled-coil forming kinase/Rho-binding kinase) such as Y-27632 to suppress cell death.

Other culture conditions (such as culture temperature) in the individual steps constituting the present invention may be conditions generally employed in culturing animal cells. That is, culture may be performed, for example, at 37° C. in an environment of 5% $CO_2$. In addition, as a basic medium, Iskov modified Dulbecco's medium (IMDM) (GIBCO-BRL or the like), Ham F12 medium. (HamF12) (SIGMA, Gibco-BRL, or the like), Dulbecco's modified Eagle's medium (D-MEM) (Nacalai Tesque Inc., Sigma-Aldrich Co. LLC, Gibco-BRL or the like), Glasgow basic medium (Gibco-BRL or the like), RPMI1640 medium, or the like can be used. Two or more basic culture media may be used in combination. In the step (1-2), the step (2), and the culture step A, the culture step B, the culture step C, and the culture step D which constitute the step (2), a basic medium suitable for culturing epithelial cells (for example, a mixed culture medium of D-MEM and Ham F12 medium and D-MEM medium) can be preferably to used. Examples of components that can be added to the culture medium include bovine serum albumin (BSA), an antibiotic, 2-mereaptoethanol, PVA, non-essential amino acids (NEAA), insulin, transferrin, and selenium. Typically, cells are two-dimensionally cultured using a culture dish or the like. According to the method of the embodiment of the present invention, an intestinal epithelial cell-like cell can be obtained from, pluripotent stem cells by two-dimensional culture. In addition, three-dimensional culture may be performed using a gel-like culture substrate or a three-dimensional culture plate.

The second aspect, of the present invention relates to the use of the intestinal epithelial cell-like cell prepared, by the differentiation induction method of the embodiment of the present invention. Various assays are provided as a first use. The intestinal epithelial cell-like cell of the embodiment of the present invention can be used for a model system of the intestinal tract, particularly the small intestine, and are useful for evaluating pharmacokinetics (absorbance, metabolism, and the like) and toxicity in the intestinal tract, particularly the small intestine. In other words, the intestinal epithelial cell-like cell of the embodiment of the present invention can be used for evaluating pharmacokinetics and toxicity of a compound.

Specifically, the intestinal epithelial cell-like cell of the embodiment of the present invention can be used to test the absorbance or membrane permeability, drag interaction, induction of a drag metabolizing enzyme, induction of a drug transporter, toxicity, or the like with respect to the test substance. That is, the present invention provides a method (first aspect) for evaluating absorbability or membrane permeability, drug interaction, induction of a drag metabolizing enzyme, induction of a drag transporter, toxicity, or the like with respect to the test substance as one of the uses of the intestinal epithelial cell-like cell. The method performs a step (i) of preparing a cell layer formed of the intestinal epithelial cell-like cells obtained by the differentiation induction method of the embodiment of the present invention, a step (ii) of bringing a test substance into contact with the cell layer; and a step (iii) of quantifying the test substance that has permeated the cell layer and evaluating absorbability or membrane permeability, drug interaction, induction of a drug metabolizing enzyme, induction of a drug transporter, or toxicity of the test substance. In addition, the absorbance of the test substance can also be evaluated by the method described below (second aspect).

In the step (i), intestinal epithelial cell-like cells are typically cultured on a semipermeable membrane (porous membrane) to form a cell layer. Specifically, for example, by using a culture vessel equipped with a culture insert (for example, Transwell (registered trademark) provided by Corning Incorporated), cells are seeded and cultured in the culture insert, and then a cell layer constituted of the intestinal epithelial cell-like cells are obtained.

The "contact" in the step (ii) is typically performed by adding a test substance to a culture medium. The timing for adding the test substance is not particularly limited. Therefore, a test substance may be added at a certain time point after starting culture in a culture medium containing no test substance, or the culture may be started in a culture medium, containing the test substance in advance.

As the test substance, an organic compound or an inorganic compound having various molecular sizes can be used. Examples of the organic compounds include a nucleic acid, a peptide, a protein, a lipid (a simple lipid, a complex lipid (a phosphoglyeeride, a sphingolipid, a glycosylglyceride, a cerebrosides, or the like), a prostaglandin, an isoprenoid, a terpene, a steroid, a polyphenol, a catechin, a vitamin (B1, B2, B3, B5, B6, B7, B9, B12, C, A, D, E, or the like). Existing components or candidate components such as a pharmaceutical, a nutritional food, a food additive, a pesticide, and perfumery (a cosmetic) are also one of the suitable test substances. A plant extract, a cell extract, a culture supernatant or the like may be used as the test substance. By adding two or more test substances at the same time, the interaction, the synergism, or the like between the test substances may be examined. The test substance may be of natural origin or synthetic. In the latter case, an efficient assay system can be constructed using, for example, a combinatorial synthesis technique.

The period for bringing the test substance into contact can be appropriately set. The contact period is, for example, 10 minutes to 3 days and preferably 1 hour to 1 day. The contact may be performed a plurality of times.

In the step (iii), the test substance that has permeated the cell layer is quantified. For example, in a case where a culture vessel equipped with a culture insert such as Transwell (registered trademark) is used, a test substance that has permeated the culture insert, that is, the test substance that has moved into the upper or lower vessel via the cell layer is quantified depending on the test substance by a measuring method such as mass spectrometry, liquid chromatography, and immunological techniques (for example, fluorescence immunoassay (FIA method) and enzyme immunoassay method (EIA method)). Based on the quantification results (the amount of the test substance permeated the cell layer) and the amount of the test substance used (typically, the amount added to the culture medium), the absorbance or membrane permeability, drug interaction, induction of a drug metabolizing enzyme, induction of a drug transporter, or toxicity are determined and evaluated with respect to the test substance.

The present invention also provides, as another aspect (second aspect), a method for evaluating metabolism or absorbance of a test substance. In the method, a step (1) of bringing a test substance into contact with the intestinal epithelial cell-like cells obtained by the differentiation induction method of the embodiment of the present invention and a step (II) of measuring and evaluating metabolism, or absorbance, drug interaction, induction of a drug metabolizing enzyme, induction of a drug transporter, or toxicity of the test substance are performed.

The step (I), that is, the brining of the test substance into contact with intestinal epithelial cell-like cells can be performed in the same manner as in the step (ii). However, it is not essential to form a cell layer in advance.

After the step (I), the metabolism or absorbance, drug interaction, induction of a drug metabolizing enzyme, induction of a drug transporter, or toxicity is measured and evaluated with respect to the test substance (step (II)). Metabolism or the like may be measured and evaluated with no substantial time interval immediately after the step (I), that is, after bringing the test substance into contact, or the metabolism or the like may be measured and evaluated after a certain time (for example, 10 minutes to 5 hours) has passed. The measurement of metabolism can be performed, for example, by detecting a metabolite. In this case, the expected metabolite is usually qualitatively or quantitatively measured using the culture solution after the step (I) as a sample. A suitable measurement method may be selected depending on the metabolite, and, for example, mass spectrometry, liquid chromatography, and immunological techniques (for example, fluorescence immunoassay (FIA), enzyme immunoassay (EIA)), and the like can be employed.

Typically, in a case where a metabolite of a test substance is detected, it is determined or evaluated that "the test substance has been metabolized". In addition, the metabolism quantity of the test substance can be evaluated according to the amount of the metabolite.

The metabolism efficiency of the test substance may be calculated based on the detection result of the metabolite and the used amount of the test substance (typically, the amount added to the culture medium).

The metabolism of a test substance can be measured using the expression of drug metabolizing enzymes (cytochrome P450 (particularly CYP3A4), uridine diphosphate-glucuronyltransferase (particularly UGT1A8, UGT1A10), and sulfotransferase (particularly SULT1A3 or the like)) in intestinal epithelial cell-like cells as an index. The expression of drug metabolizing enzymes can be evaluated at the mRNA level or the protein level. For example, in a case where an increase in the mRNA level of a drug metabolizing enzyme is recognized, it can be determined that "the test substance has been metabolized".

Similarly, in a case where an increase in the activity of a drug metabolizing enzyme is recognized, it can be determined that "the test substance has been metabolized". Similarly to the case where the metabolite is used as an index for determination, quantitative determination or evaluation may be performed based on the expression amount of the drug metabolizing enzyme.

In order to evaluate the absorbance of a test substance, for example, the remaining amount of the test substance in the culture solution is measured. Usually, test substance is quantified using the culture solution after the step (I) as a sample. A suitable measuring method may be selected depending on the test substance. For example, mass spectrometry, liquid chromatography, and immunological techniques (for example, fluorescence immunoassay (FIA), enzyme immunoassay (EIA)), and the like can be employed. Typically, in a case where a decrease in the content of test substance in the culture solution is recognized, it is determined or evaluated that "the test substance has been absorbed". In addition, the absorbance amount or the absorbance efficiency of the test substance can be determined or evaluated depending on the degree of the decrease. The absorbance can also be evaluated by measuring the amount of the test substance incorporated into the cells.

The measurement or evaluation of the metabolism and the measurement or evaluation of the absorbance may be performed simultaneously or in parallel.

As a second use of the intestinal epithelial cell-like cell prepared by the differentiation induction method of the embodiment of the present invention, a cell preparation containing intestinal epithelial cell-like cells is provided. The cell preparation of the embodiment of the present invention is applicable to treatment of various intestinal diseases. In particular, use as a material for regeneration/reconstruction of a damaged intestinal epithelial tissue (including dysfunction) is considered. That is, contribution to regenerative medicine can be expected.

The cell preparation of the embodiment of the present invention can be prepared by, for example, suspending the intestinal epithelial cell-like cells obtained by the method of the embodiment of the present invention in a physiological saline solution or a buffer (for example, a phosphate buffer) or producing a three-dimensional tissue (organoid or spheroid) using the intestinal epithelial cell-like cells. In order to be able to administer a therapeutically effective amount of cells, a single dose may contain, for example, $1 \times 10^5$ to $1 \times 10^{10}$ cells. The cell content can be suitably adjusted in consideration of the purpose of use, the target disease, gender, age, weight, state of the affected part, cell state, and the like of the target (recipient) to be administered.

Dimethyl sulfoxide (DMSO) and serum albumin for the protection of cells, antibiotics for the prevention of bacterial contamination, and various components (vitamins, cytokines, growth factors, steroids, and the like) for the activation, proliferation, differentiation induction, or the like of cells may be contained in the cell preparation of the embodiment of the present invention. In addition, other pharmaceutically acceptable components (for example, a carrier, an excipient, a disintegrant, a buffer, an emulsifier, a suspending agent, a soothing agent, a stabilizer, a preservative, an antiseptic agent, physiological saline, and the like) may be contained in the cell preparation of the embodiment of the present invention.

EXAMPLES

Search for low-molecular weight compounds useful for promoting differentiation of human iPS cells into intestinal epithelial cells and acquiring functions of intestinal epithelial cells The following investigations were performed with an aim of establishing a method for efficiently preparing a cell (intestinal epithelial cell-like cell) showing a function more similar to the function of intestinal epithelial cells of a living body.

Example 1

1. Method (1) Cells

As human iPS cells, Windy (iPS-51) and FF-1 cell lines were used. Windy is a cell line obtained by cloning a human ES cell-like colony after octamer binding protein 3/4 (OCT3/4), sex determining region Y-box 2 (SOX2), krup-pel-like factor 4 (KLF4), and v-myc myelocytomatosis viral oncogene homolog (avian) (c-MYC) were introduced into human embryonic lung fibroblast MRC-5 using a tropic retrovirus vector and was provided by Dr. Akihiro Umezawa, National Center for Child Health and Development. Mouse feeder fibroblasts (MEF) were used as feeder cells. FF-1 cell line was provided by FUJIFILM Corporation.

(2) Medium

For MEF culture, Dulbecco's modified Eagle Medium (DMEM) containing 10% fetal bovine serum (FBS), 2 mmol/L L-glutamine (L-Glu), 1% non-essential amino acids (NEAA), 100 units/mL penicillin G, and 100 µg/mL streptomycin was used. 0.05% trypsin-ethylenediarninetetraacetie acid (EDTA) was used as a MEF detaching solution, and Cell Banker 1 was used as a MEF storage solution. For maintenance culture of Windy, DMEM Ham's F-12 (DMEM/F12) containing 20% knockout serum replacement (KSR), 0.8% NEAA, 2 mmol/L L-Glu, 0.1 mmol/L 2-mercaptoethanol (2-MeE), and 5 ng/mL fibroblast growth factor 2 (FGF2) was used. Dulbecco's phosphate buffered saline (PBS) containing 1 mg/mL collagenase IV, 0.25% trypsin, 20% KSR, and 1 mmol/L calcium chloride was as a detaching solution, and a cryopreservation liquid for primate ES/iPS cells was used as a preservation solution. mTesR1 was used for maintenance culture of the FF-1 line.

(3) Culture of Human iPS Cells

Windy was seeded on MEF ($6 \times 10^5$ cells/100 mm dish) treated with mitomycin C and cultured at 37° C. in a $CO_2$ incubator under the condition of 5% $CO_2$/95% air. The FF-1 line was cultured on a dish coated with Matrigel. Passage of human iPS cells was performed at a split ratio of 1:2 to 1:3 after culturing for 3 to 5 days. For the human iPS cells, the culture medium was changed 48 hours after thawing the cells, and thereafter changed daily.

(4) Induction of Human iPS Cell Differentiation into Intestinal Epithelial Cells Induction of differentiation of human iPS cells into intestinal epithelial cells was started in a state where undifferentiated colonies of the human iPS cells accounted for about 70% of the culture dish. Windy was induced to differentiate into endoderm by culturing for two days in Roswell Park Memorial Institute (RPMI)+Glutamax medium containing 0.5% FBS, 100 ng/mL activin A, 100 units/mL penicillin G, and 100 µg/mL streptomycin and then culturing for one day in RPMI+Glutamax medium, containing 2% FBS, 100 ng/mL activin A, 100 units/ml penicillin G, and 100 µg/mL streptomycin. Then, the cells were cultured in DMEM/F12 containing 2% FBS, 1% Glutamax, and 250 ng/mL FGF2 for 4 days to induce differentiation into intestinal stem cells. After this treatment, Y-27632 (Rho-binding kinase inhibitor) was added so that the concentration was 10 µmol/L, and the cells treated at 37° C. for 60 minutes in a $CO_2$ incubator under the condition of 5% $CO_2$/95% air were treated with actase for detaching. The detached cells were seeded on a 24-well cell culture plate coated with Matrigel which was diluted 30-fold with a human iPS cell culture medium and from which growth factors was removed. Thereafter, the intestinal stem cells were cultured to induce differentiation into intestinal epithelial cells for one day in DMEM/F12 containing 2% FBS, 1% Glutamax, 1% NEAA, 2% B27 supplement, 1% N2 supplement, 100 units/mL penicillin G, 100 µg/mL streptomycin, 20 ng/mL epidermal growth factor (EGF), and 10 µmol/L Y-27632, and 18 days in DMEM/F12 containing 2% FBS, 1% Glutamax, 1% NEAA, 2% B27 supplement, 1% N2 supplement, 100 units/mL penicillin G, 100 µg/mL streptomycin, and 20 ng/mL epidermal growth factor (EGF). In addition, in addition to PD98059 (20 µmol/L), 5-aza-2'-deoxycytidine (5 µmol/L), and A-83-01 (0.5 µmol/L) which are low-molecular weight compounds previously discovered by the present inventors during differentiation induction, 1 mmol/L 8-Bromoadenosine-3',5'-cyclic monophosphate (8-Br-cAMP), 0.1 or 0.5 mmol/L 3-isobutyl-1-methylxanthine (IBMX), or 10 or 30 µmol/L Forskolin was added to investigate the effect on the induction of differentiation into intestinal stem cells and intestinal epithelial cells.

Figure 4:
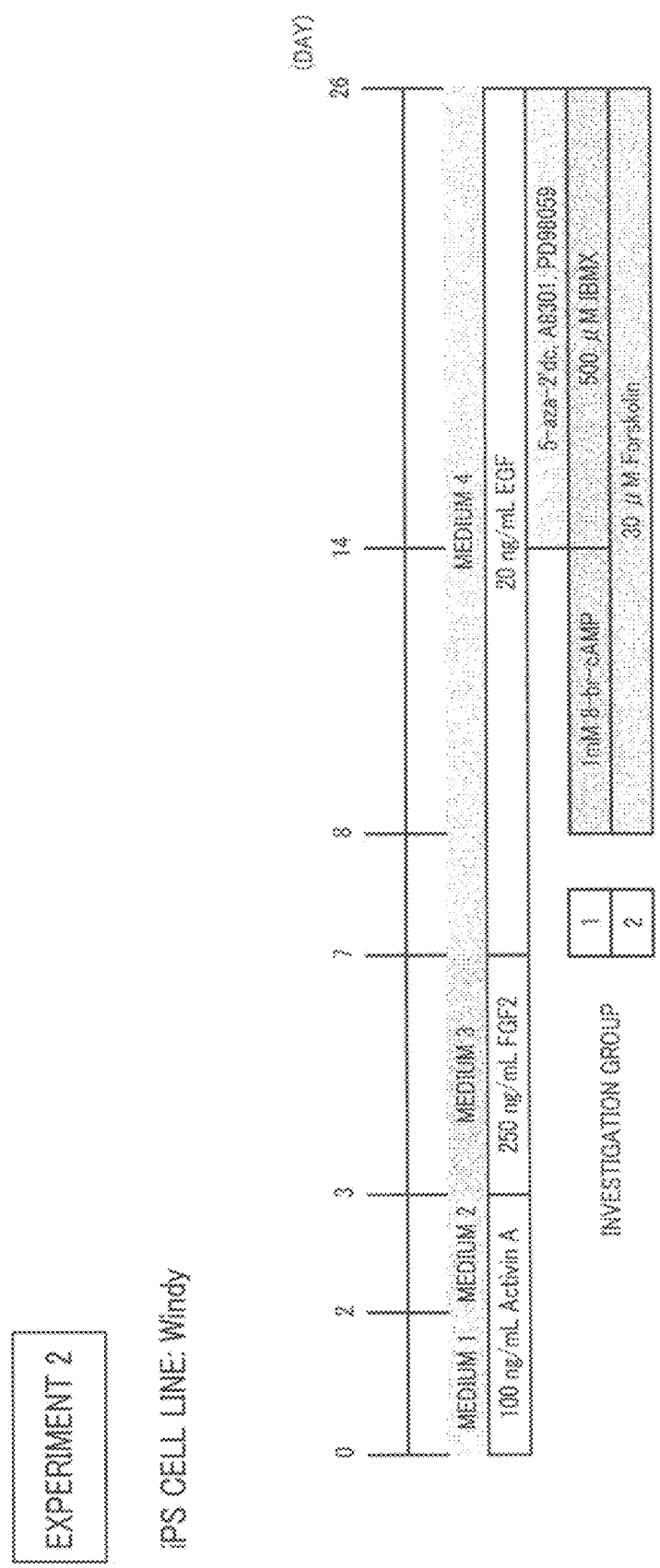
FIG. 4. Protocol of experiment 2 using human iPS cells (Windy). After inducing differentiation into intestinal stem cells by culturing for 3 days (day 0 to day 3) in the presence of Activin A and for 4 days (day 3 to day 7) in the presence of FGF2, the cells were induced to differentiate into intestinal epithelial cells by culturing for 18 days (day 8 to day 26). The following test groups 1 and 2, in which the components added to the culture medium, during inducing differentiation into intestinal epithelial cells were different, were set up, and the effects on differentiation were compared. Test group 1 in which 8-Br-cAMP was added to the culture medium from day 8 to day 14 and IBMX was added to the culture medium from day 14 to day 26, and test group 2 in which Forskolin was added to the culture medium from day 8 to day 26.
Figure 6:
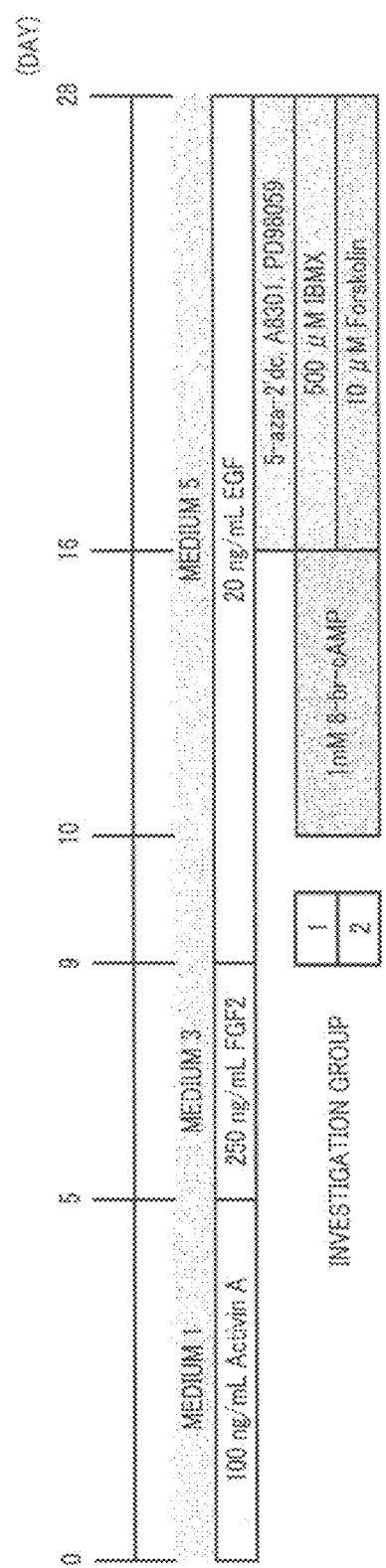
FIG. 6. Protocol of experiment 3 using human iPS cells (FF-1). After inducing differentiation into intestinal stem cells by culturing for 5 days (day 0 to day 5) in the presence of Activin A and for 4 days (day 5 to day 9) in the presence of FGF2, the cells were induced to differentiate into intestinal epithelial cells by culturing for 18 days (day 10 to day 28). The following test groups 1 and 2, in which the components added to the culture medium during inducing differentiation into intestinal epithelial cells were different, were set up, and the effects on differentiation were compared. Test group 1 in which 8-Br-cAMP was added to the culture medium from day 10 to day 16 and IBMX was added to the culture medium from day 16 to day 28, and test group 2 in which 8-Br-cAMP was added to the culture medium from day 10 to day 16 and Forskolin was added to the culture medium from day 16 to day 28.
Figure 9:
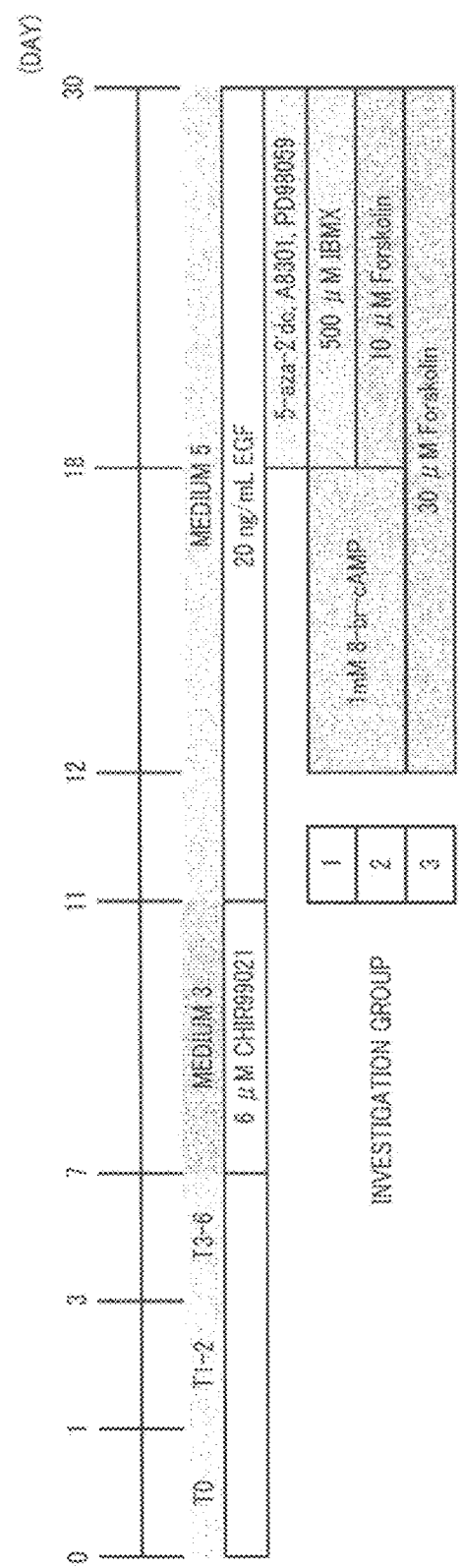
FIG. 9. Protocol of experiment 4 using human iPS cells (FF-1). After inducing differentiation into intestinal stem cells by culturing in the presence of A Activin A and culturing in the presence of BMP4, VEGF, FGF2, and EGF for 7 days (day 0 to day 7) in total and for 4 days (day 7 to day 11) in the presence of CHIR99021, the cells were induced to differentiate into intestinal epithelial cells by culturing for 18 days (day 12 to day 30). The following test groups 1 to 3, in which the components added to the culture medium during inducing differentiation into intestinal epithelial cells were different, were set up, and the effects on differentiation were compared. Test group 1 in which 8-Br-cAMP was added to the culture medium from, day 12 to day 18 and IBMX was added to the culture medium from, day 18 to day 30, and test group 2 in which 8-Br-cAMP was added to the culture medium from day 12 to day 18 and Forskolin was added to the culture medium from day 18 to day 30, and test group 3 in which Forskolin was added to the culture medium from day 12 to day 30.

Experiment 1 (FIG. 1) and experiment 2 (FIG. 4) using Windy and experiment 3 (FIG. 6), experiment 4 (FIG. 9), and experiment 5 (FIG. 11) using the FF-1 line were set. In experiment 3, the FF-1 strain was cultured for 5 days (day 0 to 5) to induce differentiation into endoderm, 4 days (day 5 to 9) to induce differentiation into intestinal stem cells, and 18 days (day 10 to 28) to induce differentiation into intestinal epithelial cells. In experiment 4, the FF-1 strain was cultured for 7 days (day 0 to 7) to induce differentiation into endoderm, 4 days (day 7 to day 11) to induce differentiation into intestinal stem cells, and 18 days (day 12 to day 30) to induce differentiation into intestinal epithelial cells. In experiment 5, the FF-1 strain was cultured for 7 days (day 0 to day 7) to induce differentiation into endoderm, 4 days (day 7 to day 11) to induce differentiation into intestinal stem cells, and 18 days (day 12 to day 30) to induce differentiation into intestinal epithelial cells. The induction of differentiation into endoderm in experiment 4 and experiment 5 was performed according to the method described in WO2014/165663A (specifically, Examples 1 and 5).

(5) Total Ribonucleic Acid (RNA) Extraction

After completing the induction of differentiation of human iPS cells, total RNA was extracted according to the attached manual of RNeasy (registered trademark) Mini Kit (Qiagen).

(6) Reverse Transcription Reaction

For synthesis of complementary DNA (cDNA), ReverTra Ace (registered trademark) qPCR RT Kit (Toyobo Co., Ltd.) was used. The operation followed the attached manual.

(7) Real-Time Reverse Transcriptase Polymerase Chain Reaction (Real-Time RT-PCR)

Real-Time RT-PCR was performed using cDNA as a template with KAPA SYBR Fast qPCR Kit (Nippon Genetics Co., Ltd.). The operation followed the attached manual. The measurement results were corrected using hypoxanthine-guanine phosphoribosyltransferase (HPRT) as an internal control.

(8) Drug Metabolism Experiment

After completing the differentiation induction, the differentiated cells were cultured at 37° C. in a culture medium (DMEM/F12 containing 1% Glutamax, 1% NEAA, 1% N2 supplement, 100 units/mL penicillin G, 100 µg/mL streptomycin, and 20 ng/mL EGF) containing 5 µmol/L midazolam and 10 µmol/L 7-hydroxycoumarin, and the culture medium was sampled after 24 hours (experiments 3 and 4) or 2 hours (experiment 5). The metabolic activity was calculated from the amount of 1-hydroxymidazolam or 7-hydroxycoumarin glucuronide in the culture medium, which was measured using a liquid chromatography-mass spectrometer (LC-MS/MS). After completing the metabolic experiment, protein quantification was performed, and the metabolic activity was corrected with the amount of protein.

The characteristics of the marker genes used in the present investigations are described below.

ABCB1/MDR1 (ATP-binding cassette transporter B1/multidrug resistance protein 1): A P-glycoprotein that functions as an efflux transporter.

CYP3A4 (cytochrome P4503A4): A major drug metabolizing enzyme in the small intestine.

FABP (fatty acid binding protein 2): Various subtypes are present, and FABP2 is intestinal.

PXR (pregnane X receptor): Involved in expression and induction of CYP3A4.

SLC5A1/SGLT1 (SLC (solute carrier) family member 5A1/sodium conjugated glucose transporter 1): A glucose transporter expressed on the apical membrane side of the small intestine.

SLC15A1/PEPT1 (SLC (solute carrier) family member 15A1/peptide transporter 1): Expressed on the apical membrane side of the small intestine.

Villin1: A major component of microvilli.

CES2A1: Carboxylesterase 2A1. CES which is a hydrolase has isoforms of 1A and 2A1, with high expression of CES1A in the liver and high expression of CES2A1 in the small intestine.

Figure 3:
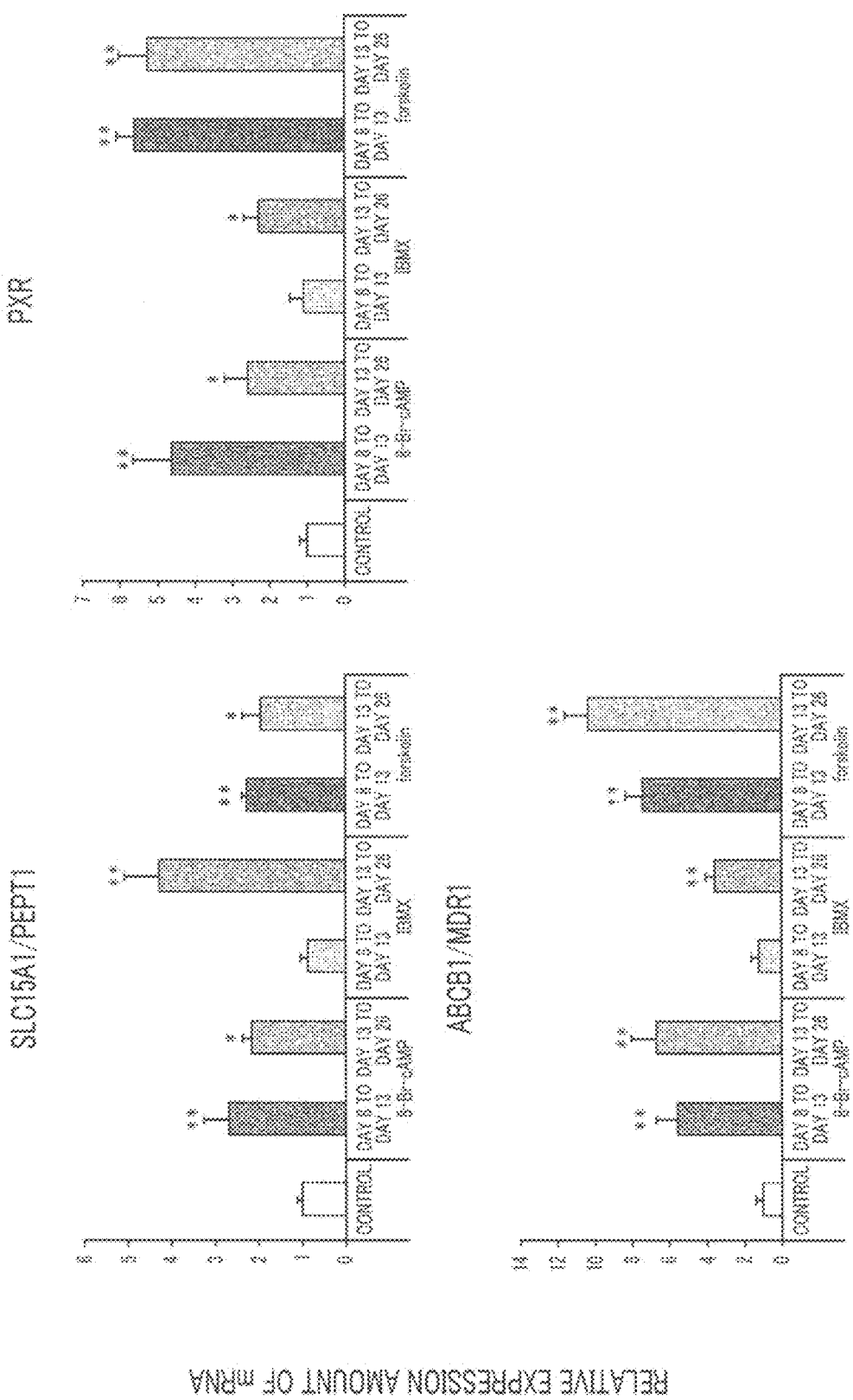
FIG. 3. Continuation of FIG. 2.
Figure 5:
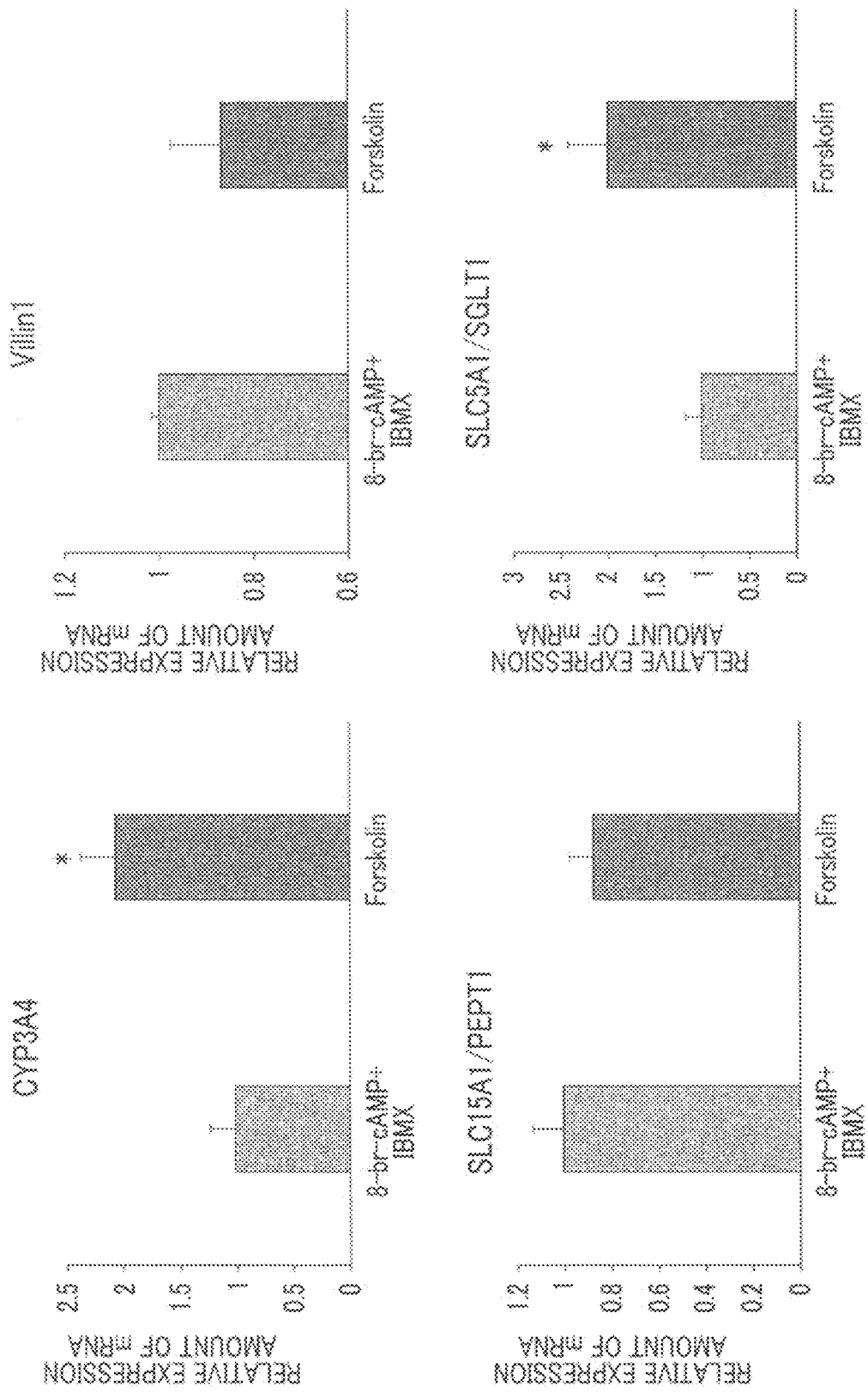
FIG. 5. Effect of cAMP activator (Forskolin) on induction of differentiation of human iPS cells into intestinal epithelial cells (result of experiment 2). The expression amounts of various marker genes were compared. The expression amounts were represented by the average value±S.D. (n=3). * $P<0.05$ vs 8-Br-cAMP added and IBMX added groups.

2. Result (1) Investigation of Effects on Inducing Differentiation into Intestinal Epithelial Cells Addition of Forskolin on day 8 after the start of differentiation significantly increased the gene expression levels of various intestinal markers (FIGS. 2 and 3). The effect of Forskolin on intestinal tract marker expression tended to be similar to that of 8-Br-cAMP, which the present inventors have found so far, but the effect of Forskolin on the expressions of CYP3A4 which is a major drug metabolizing enzyme and ABCB1/MDR1 which is important as an efflux transporter drastically exceeded that of 8-Br-cAMP. In addition, in comparison with the differentiation induction method using 8-Br-cAMP and IBMX in combination, which has been developed by the inventors, differentiation with Forskolin alone significantly increased the expression level of CYP3A4 and SGLT1 which are particularly important as intestinal epithelial cell markers (FIG. 5). As a result, it was suggested that Forskolin was extremely effective in promoting differentiation of human iPS cells into intestinal epithelial cells.

Figure 7:
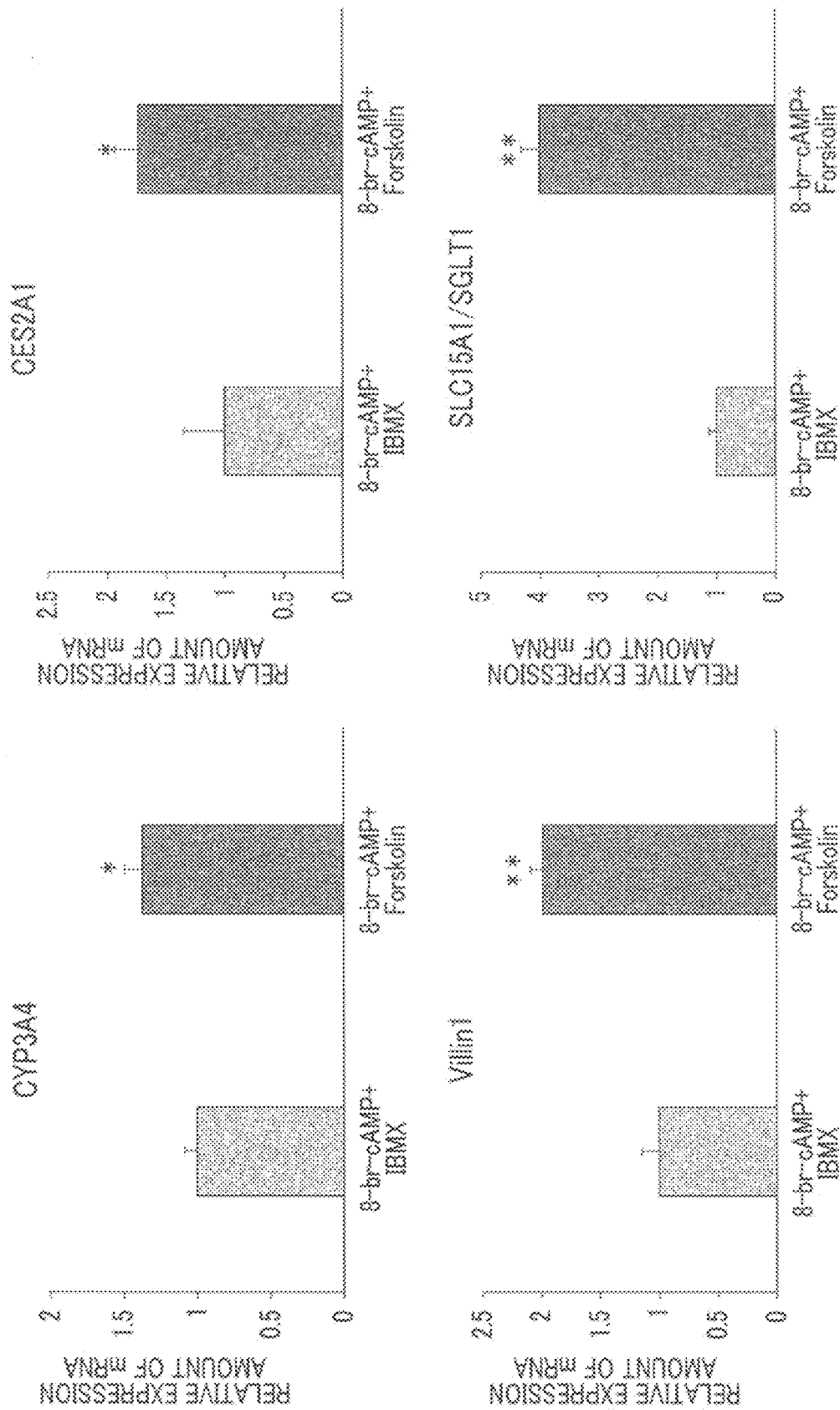
FIG. 7. Effect of cAMP activator (Forskolin) on induction of differentiation of human iPS cells into intestinal epithelial cells (result of experiment 3). The expression amounts of various marker genes were compared. The expression amounts were represented by the average value±S.D. (n=3). * $P<0.05$ vs 8-Br-cAMP added and IBMX added groups, ** $P<0.01$ vs 8-Br-cAMP added and IBMX added groups.
Figure 8:
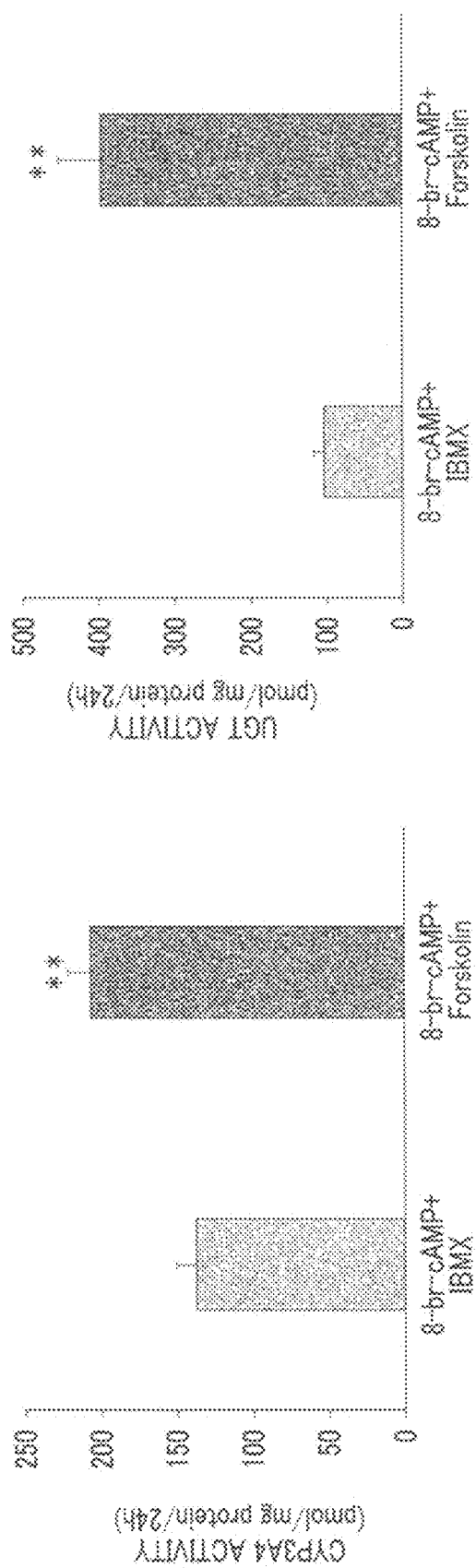
FIG. 8. Effect of cAMP activator (Forskolin) on drug metabolizing enzyme activity of intestinal epithelial cell-like cells derived from, human iPS cells (result of experiment 3). The expression amounts were represented by the average value±S.D. (N=4). * $P<0.01$ vs 8-Br-cAMP added and IBMX added groups.
Figure 10:
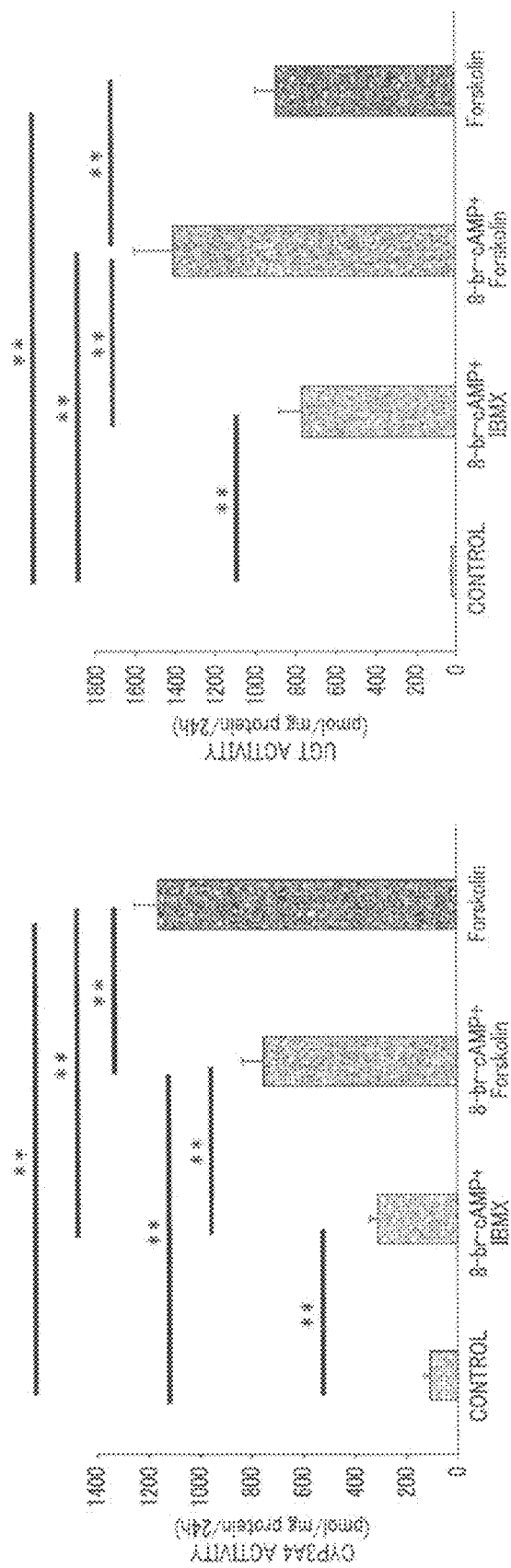
FIG. 10. Effect of cAMP activator (Forskolin) on drug metabolizing enzyme activity of intestinal epithelial cell-like cells derived from human iPS cells (result of experiment 4). The expression amounts were represented by the average value±S.D. (N=4). * $P<0.01$ vs control group. The control group is a group in which additional components (8-Br-cAMP, IBMX, Forskolin) were not added.
Figure 11:
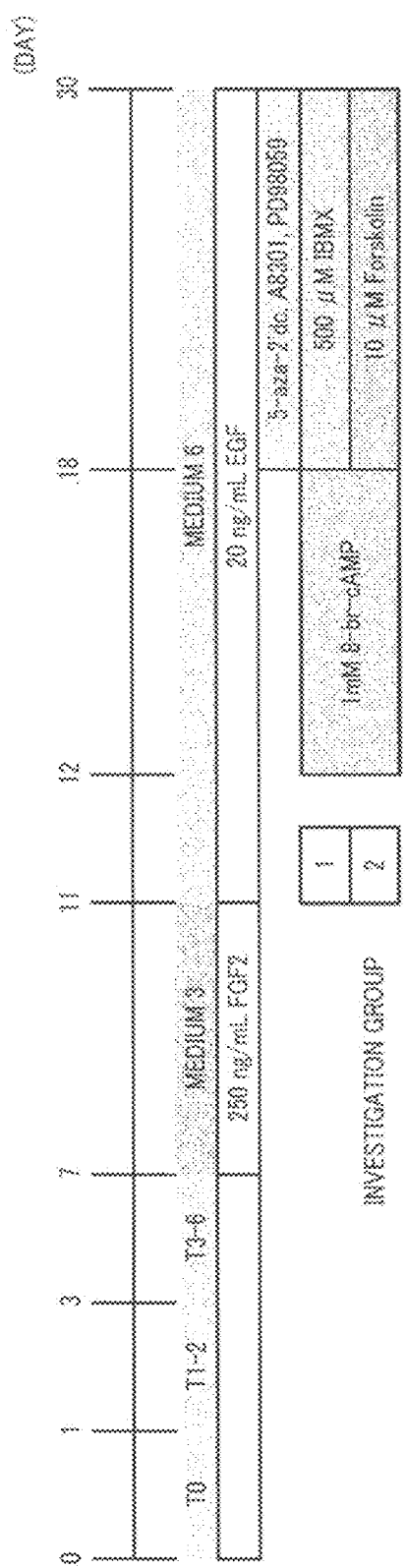
FIG. 11. Protocol of experiment 5 using human iPS cells (FF-1). After inducing differentiation into intestinal stem cells by culturing in the presence of A Activin A and culturing in the presence of BMP4, VEGF, FGF2, and EGF for 7 days (day 0 to day 7) in total and for 4 days (day 7 to day 11) in the presence of FGF2, the cells were induced to differentiate into intestinal epithelial cells by culturing for 18 days (day 12 to day 30). The following test groups 1 to 2, in which the components added to the culture medium during inducing differentiation into intestinal epithelial cells were different, were set up, and the effects on differentiation were compared. Test group 1 in which 8-Br-cAMP was added to the culture medium from day 12 to day 18 and IBMX was added to the culture medium from day 18 to day 30. Test group 2 in which 8-Br-cAMP was added to the culture medium from day 12 to day 18 and Forskolin was added to the culture medium from day 18 to day 30.
Figure 12:
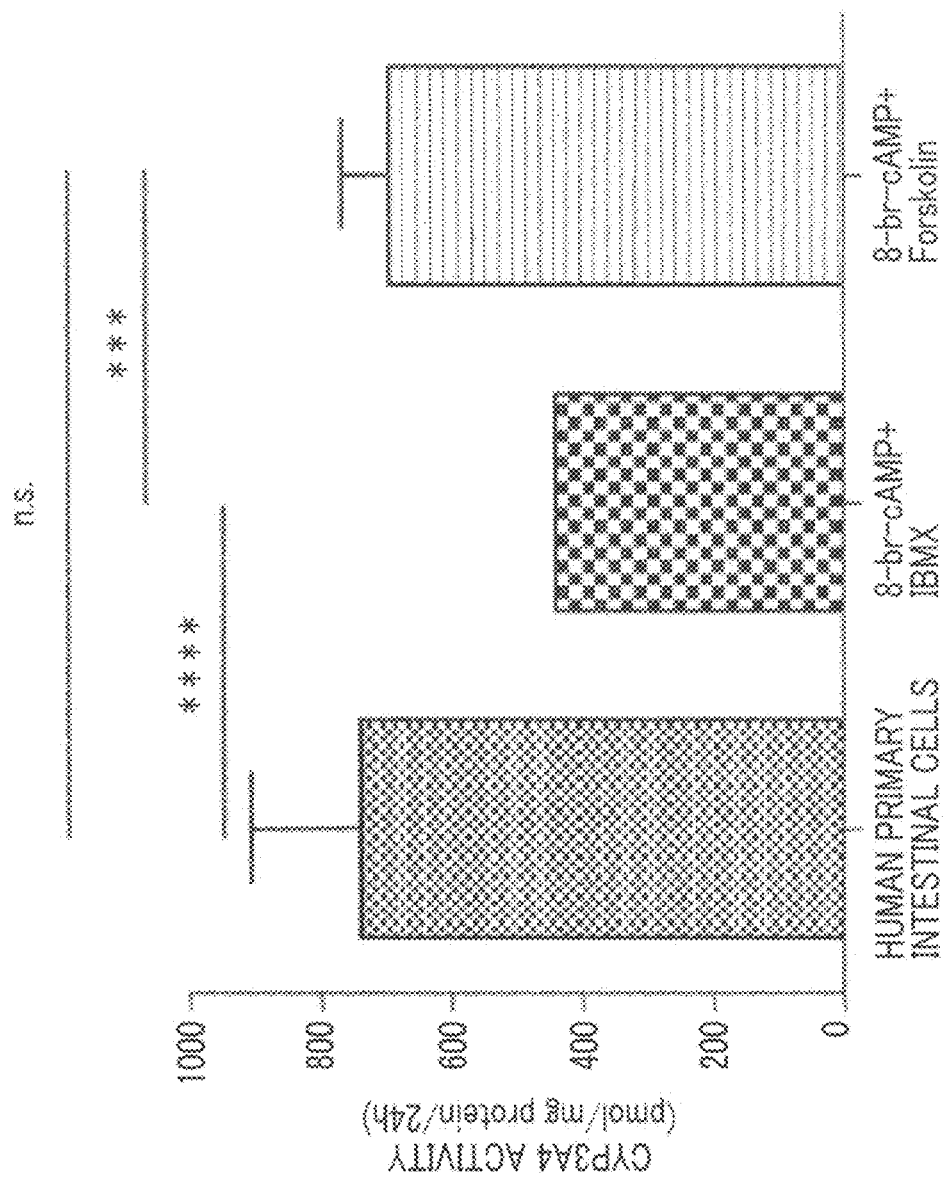
FIG. 12. Effect of cAMP activator (Forskolin) on drug metabolizing enzyme activity of intestinal epithelial cell-like cells derived from human iPS cells (result of experiment 5). The expression amounts were represented by the average value±S.D. (n=3). ** $P<0.0001$ for human primary small intestinal cells vs test group 1, $_{ns}P>0.05$ for human primary small intestinal cells vs test group 2, * $P≤0.001$ for test group 1 vs test group 2. Human primary small intestinal cells (Lot No. HE3007, In Vitro ADMET Laboratories) were used.

(2) Effect on Drug Metabolizing Enzyme Activity in Intestinal Epithelial Cell-Like Cell Derived from iPS Cells In comparison with the differentiation using 8-Br-cAMP and IBMX, the differentiation using 8-Br-cAMP and Forskolin significantly increases the gene expression levels of various intestinal markers (FIG. 7), and activities of CYP3A4 and UGT were significantly increased (FIG. 8). Further, in a case where Forskolin was used instead of 8-Br-cAMP for a long period from day 12 after the initiation of differentiation induction, a further significant increase in the CYP3A4 activity was observed (FIG. 10). Regarding the UGT activity, the metabolic activity was the highest in a group differentiated with 8-Br-cAMP and Forskolin (FIG. 10). Further, in a group differentiated into intestinal stem cell-like cells using FGF2 and differentiated into intestinal epithelial-like cells using 8-Br-cAMP and Forskolin, a CYP3A4 activity similar to that of human primary small intestinal cells was observed (FIGS. 11 and 12). This observation suggested that Forskolin may contribute not only to gene expression of intestinal markers but also to pharmacokinetic functions such as drag metabolizing enzyme activity.

By using Forskolin to induce differentiation of human iPS cells into intestinal epithelial cells, the metabolic activity by CYP3A4, which is particularly important among drug metabolizing enzymes expressed in the small intestine, was greatly increased in addition to increasing the expression level of particularly important intestinal epithelial cell markers. In addition, this method has a higher effect on metabolic enzyme activity than the method previously discovered by the inventors. In applying these cells to drug discovery research, the differentiation induction method that can obtain the above-described effects in terms of function is considered to be an extremely useful method.

3. Conclusion

Based on the above results, a method for producing a further matured intestinal epithelial cell-like cell from human iPS cells was established. In addition, it has been found that these cells have sufficient drug metabolizing activity by CYP3A4 and the like and CYP3A4 activity thereof is similar to that of human primary small intestinal cells. Since Caco-2 cells, which are currently widely used as a test system for gastrointestinal absorbance of a drug, have a problem of low drug metabolizing activity, it is thought that the present invention enables the production of cells having a function similar to that of the human small intestine.

Example 2

1. Method (1) Differentiation of Human iPS Cells into Small Intestinal Epithelial Cells Human iPS cells (FF-1) were treated with a serum-free medium containing 100 ng/mL activin A for 24 hours to initiate differentiation. Thereafter, the cells were treated in a serum-free medium containing 100 ng/mL activin A, 2.5 ng/mL BMP4, 10 ng/mL VEGF, and 5 ng/mL FGF2 for 144 hours to differentiate into endoderm. Thereafter, the cells were cultured in Advanced DMEM/F-12 containing 2% FBS, 1% GlutaMax, 100 units/mL penicillin G, 100 µg/mL streptomycin sulfate, and 250 ng/mL FGF2 for 96 hours to differentiate into small intestine stem cells. The small intestine stem cell-like cells after the treatment with activin A and FGF2 were detached with Aecutase and seeded on GFR Matrigel which was diluted 30-fold with human iPS medium in advance. After seeding, the cells were cultured for 19 to 23 days in Advanced DMEM/F-12 containing 2% FBS, 0.1 mM NEAA, 2 mM L-Glu, 100 units/mL penicillin G, 100 µg/mL streptomycin sulfate, 2% B27 supplement, 1% N2 supplement, 1% HepExtend supplement, 20 ng/mL EGF, and 30 µM Forskolin. From 12 to 16 days before the end of differentiation, differentiation into small intestinal epithelial cells was induced was by adding PD98059 to 20 µM, 5-aza-2'-deoxycytidine (5-aza-2'-dC) to 5 µM, and A-83-01 to 0.5 µM.

(2) Membrane Permeation Test

HESS (pH 6.5) was added to a chamber on the apical side of human iPS cell-derived small intestinal epithelial cells and Caco-2 cells seeded on Cell culture insert, HBSS (pH 7.4) was added to a chamber on the basal side, and pre-incubated at 37° C. for 60 minutes. Then, HBSS (pH 6.5) containing acebutolol, metformin, hydrochlorothiazide, sulpiride, and lucifer yellow which are compounds permeating paracellularly, cephalexin, lisinopril, ribavirin, and enalapril which are compounds permeating via transporters, antipyrine and caffeine which are compounds permeating transcellularly, and erythromycin, indinavir, midazolam, tacrolimus, and verapamil which are substrates of CYP3A4 was added to the chamber on the apical side and incubated at 37° C. for 60 minutes. Each compound was added so that the final concentrations of lisinopril and caffeine were 50 µM, the final concentration of lucifer yellow was 50 µg/mL, and the final concentrations of the other compounds were 10 µM. In addition, HBSS (pH 7.4) was added to the chamber on the basal side. A sample was collected from the receiver chamber every 15 minutes. The unchanged substance was measured using UPLC-MS/MS. $F_a \cdot F_g$ in humans was referred from, previous reports (References 1 to 6 below).

Reference 1: Takenaka T, Harada N, Kuze J, Chiba M, Iwao T, Matsunaga T. Human small intestinal epithelial cells differentiated from adult intestinal stem cells as a novel system for predicting oral drug absorption in humans. Drug Metab Dispos. 42: 1947-54 (2014).

Reference 2: Takenaka T, Harada N, Kuze J, Chiba M, Iwao T, Matsunaga T. Application of a Human Intestinal Epithelial Cell Monolayer to the Prediction of Oral Drug Absorption in Humans as a Superior Alternative to the Caco-2 Cell Monolayer. J Pharm Sci. 105: 915-924 (2016).

Reference 3: Tachibana T, Kato M, Sugiyama Y. Prediction of nonlinear intestinal absorption of CYP3A4 and P-glycoprotein substrates from their in vitro Km values. Pharm Res. 29: 651-68 (2012).

Reference 4: Chong S, Dando S A, Soucek K M, Morrison R A. In vitro permeability through caco-2 cells is not quantitatively predictive of in vivo absorption for peptide-like drugs absorbed via the dipeptide transporter system. Pharm Res. 13: 120-3 (1996).

Reference 5: Zhu C, Jiang L, Chen T M, Hwang K K. A comparative study of artificial membrane permeability assay for high throughput profiling of drug absorption potential. Eur J Med Chem. 37: 399-407 (2002).

Reference 6: Cheng K C, Li C, Uss A S. Prediction of oral drug absorption in humans—from cultured cell lines and experimental animals. Expert Opin Drug Metab Toxicol. 4: 581-90 (2008).

The correlation of 11 compounds excluding the CYP3A4 substrate with $P_{app}$ and human $F_a \times F_g$ was analyzed by the nonlinear least squares method using the following expression. The analysis method referred to the existing report (Reference 2 described above).

$$F_a = 1 - e^{-P(1) \cdot P_{app}}$$

Here, P(1) is a scaling factor. WinNonlin (Certara, USA) was used for nonlinear regression analysis. Correlation coefficient (R values) was calculated to evaluate the correlation between $P_{app}$ in human iPS cell-derived small intestinal epithelial cells and Caco-2 cells and human $F_a \cdot F_g$.

Figures 14A, 14B:
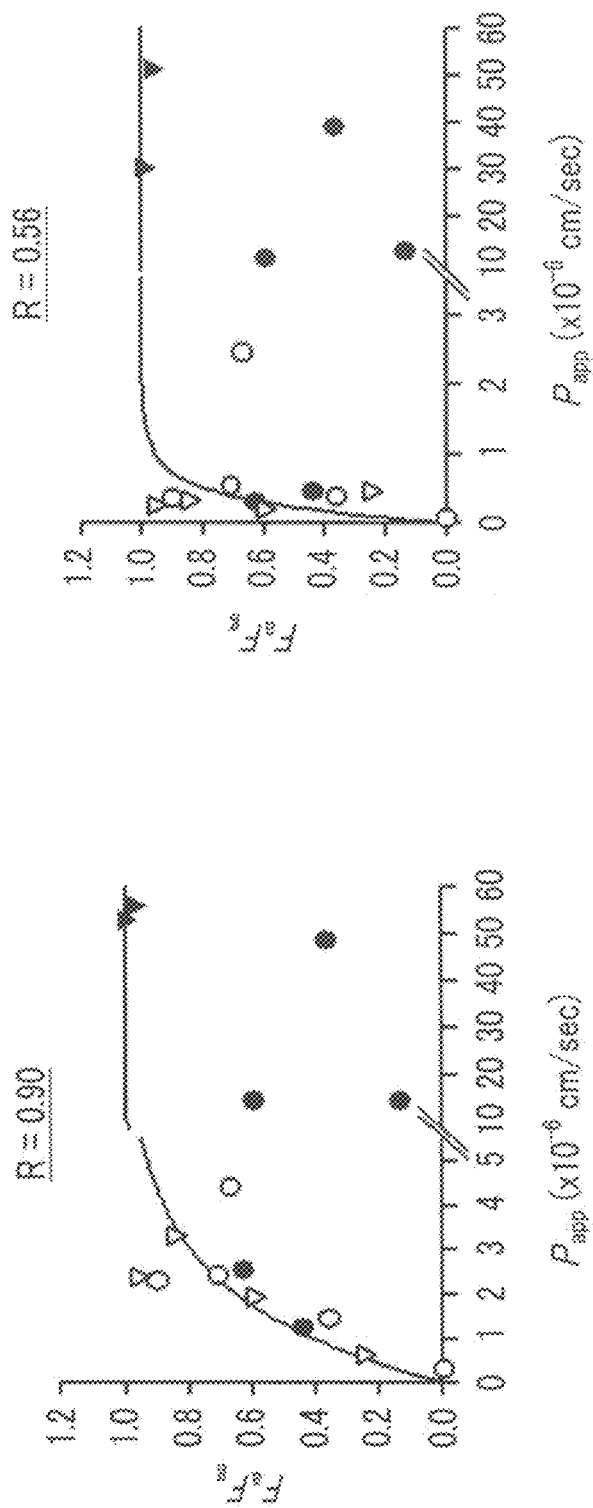
FIGS. 14A and 14B. Relationship between $F_a$ value and $P_{app}$ of 16 kinds of drugs. Differentiated small intestinal cells (A) and Caco-2 cells (B) were incubated in a transport buffer containing 16 kinds of drugs at 37° C. for 60 minutes. The correlation curve was fitted using the following expression. $F_a=1-e^{P(1)\times Papp}$. The P(1) values of the differentiated small intestinal cells (A) and Caco-2 cells (B) were respectively 0.531±0.083 and 3.243±0.992. All data are shown as mean±standard deviation (n=3).

2. Result (1) Membrane Permeation Characteristics of Small Intestinal Epithelial Cells Derived from Human iPS Cell Line In order to verify whether $F_a \cdot F_g$ in humans can be predicted from $P_{app}$ of the results of a membrane permeation test of small intestinal epithelial cells derived from human iPS cell line, $P_{app}$ and $F_a \cdot F_g$ of 16 compounds were compared (Table 1). The correlation between $P_{app}$ and $F_a \cdot F_g$ of 11 compounds excluding the CYP3A4 substrate in human iPS cell-derived small intestinal epithelial cells and Caco-2 cells was analyzed by the nonlinear least squares method, and the regression curves shown in FIGS. 14A and 14B were obtained. The scaling factors of human iPS cell-derived small intestinal epithelial cells and Caco-2 cells were respectively 0.531±0.083 and 3.243±0.992. $P_{app}$ of a compound that passes through the intercellular pathway and a compound that is transported by a transporter gradually increased as the value of $F_a \cdot F_g$ increased in human iPS cell-derived small intestinal epithelial cells. However, in Caco-2 cells, $P_{app}$ showed almost the same value even in the case of compounds having different $F_a \cdot F_g$ (FIGS. 14A and 14B). The correlation coefficient between $P_{app}$ and $F_a \cdot F_g$ in 11 compounds excluding the CYP3A4 substrate was 0.9 in human iPS cell-derived small intestinal epithelial cells and 0.56 in Caco-2 cells, and intestinal epithelial cells derived from human iPS cells had higher correlation with human $F_a \cdot F_g$.

[Table 1]

TABLE 1

$P_{app}$ values of differentiated intestinal cells and Caco-2 cells. Cells were incubated for 60 minutes at 37° C. in a transport buffer containing a plurality of drugs. All data are shown as mean ± standard deviation (n = 3).

| | $F_a \cdot F_g/100$ (%) | $P_{app}$ of intestinal cells (×10⁶ cm/sec) | $P_{app}$ of Caco-2 cells (×10⁶ cm/sec) |
|---|---|---|---|
| Acebutolol | 0.9 | 2.3 | 0.35 |
| Metformin | 0.71 | 2.43 | 0.52 |
| Hydrochlorothiazide | 0.67 | 4.4 | 2.44 |
| Sulpiride | 0.36 | 1.45 | 0.36 |
| Lucifer yellow | 0 | 0.3 | 0.06 |
| Cephalexin | 0.96 | 2.36 | 0.23 |
| Lisinopril | 0.25 | 0.63 | 0.44 |
| Ribavirin | 0.85 | 3.3 | 0.32 |
| Enalapril | 0.6 | 1.93 | 0.19 |
| Antipyrine | 0.97 | 55.62 | 51.32 |
| Caffeine | 1 | 52.39 | 30.12 |
| Erythromycin | 0.441 | 1.24 | 0.45 |
| Indinavir | 0.63 | 2.54 | 0.28 |
| Midazolam | 0.369 | 48.34 | 38.74 |
| Tacrolimus | 0.136 | 14.32 | 12.29 |
| Verapamil | 0.595 | 14.22 | 10.65 |

3. Consideration

According to the results of the membrane permeation test, various compounds transported via intercellular pathway or by a transporter and having different $F_a \cdot F_g$ were permeated at the similar rate in Caco-2 cells, but the compounds were permeated at different rates depending on the value of $F_a \cdot F_g$ in human iPS cell-derived small intestinal epithelial cells (FIGS. 14A and 14B). As a result, $P_{app}$ in human iPS cell-derived small intestinal epithelial cells showed higher correlation with $F_a \cdot F_g$ than Caco-2 cells. This is probably because Caco-2 cells have strong tight junctions and thus the permeability of drugs via intercellular pathways is low and the expression of transporters is low. From the above results, it was suggested that the membrane permeation of a substrate passing via the intercellular pathway and a substrate transported by a transporter be predicted better in human iPS cell-derived small intestinal epithelial cells than in Caco-2 cells.

According to the present invention, more functional intestinal epithelial cell-like cell can be prepared simply and efficiently from, pluripotent stem cells. The intestinal epithelial cell-like cells is useful as a model system for the small intestine, and can be used for absorbance, metabolism, membrane permeability, induction of a drug metabolizing enzyme, induction of a drug transporter, evaluation of toxicity, and the like. It is also expected to be used as an active component of cell preparations for treating various intestinal diseases or as a material for regenerative medicine.

The present invention is not limited to the description of the embodiment and Examples of the invention described above. Various modifications are included in the present invention without departing from the scope of what is claimed and within the scope of those skilled in the art. The contents of articles, published unexamined patent applications, and patent publications specified in the present specification are ail incorporated by reference.

What is claimed is:

1. A method for inducing differentiation of pluripotent stem cells into intestinal epithelial cell-like cells, the method comprising the following steps (1) and (2):
   the step (1) of differentiating pluripotent stem cells into intestinal stem cell-like cells; and
   the step (2) of differentiating the intestinal stem cell-like cells obtained in the step (1) into intestinal epithelial cell-like cells by using an MEK1 inhibitor, a DNA methylation inhibitor, a TGFβ receptor inhibitor, EGF, and a cAMP activator in combination,
   wherein the pluripotent stem cells are induced pluripotent stem cells, the cAMP activator is Forskolin or NKH477, and the step (1) consists of the following steps (1-1) and (1-2):
   the step (1-1) of differentiating induced pluripotent stem cells into endoderm-like cells; and
   the step (1-2) of differentiating the endoderm-like cells obtained in the step (1-1) into intestinal stem cell-like cells.

2. The method according to claim 1,
   wherein a culture period in the step (2) is 7 days to 40 days.

3. The method according to claim 1,
   wherein the step (2) includes any one of the following culture steps A to D,
   the culture step A including a culturing (a-1) in a presence of the EGF and the CAMP activator and a culturing (a-2), which is performed after the culturing (a-1), in a presence of the MEK1 inhibitor, the DNA methylation inhibitor, the TGFβ receptor inhibitor, and the EGF,
   the culture step B including a culturing (b-1) in a presence of the EGF and a culturing (b-2), which is performed after the culturing (b-1), in a presence of the MEK1 inhibitor, the DNA methylation inhibitor, the TGFβ receptor inhibitor, the EGF, and the cAMP activator,
   the culture step C including a culturing (c-1) in a presence of the EGF and the CAMP activator and a culturing (c-2), which is performed after the culturing (c-1), in a presence of the MEK1 inhibitor, the DNA methylation inhibitor, the TGFβ receptor inhibitor, the EGF, and the cAMP activator, and
   the culture step D including a culturing (d-1) in a presence of the MEK1 inhibitor, the DNA methylation inhibitor, the TGFβ receptor inhibitor, the EGF, and the cAMP activator.

4. The method according to claim 3,
   wherein a period of the culturing (a-1) is 2 days to 10 days, a period of the culturing (a-2) is 9 days to 29 days,
   a period of the culturing (b-1) is 2 days to 10 days, a period of the culturing (b-2) is 9 days to 19 days,
   a period of the culturing (c-1) is 2 days to 10 days, a period of the culturing (c-2) is 9 days to 19 days, and
   a period of the culturing (d-1) is 15 days to 25 days.

5. The method according to claim 3,
   wherein the culture step B includes a culturing (b-3), which is performed after the culturing (b-2), in a presence of the MEK1 inhibitor, the DNA methylation inhibitor, the TGFβ receptor inhibitor, and the EGF, the culture step C includes a culturing (c-3), which is performed after the culturing (c-2), in a presence of the MEK1 inhibitor, the DNA methylation inhibitor, the TGFβ receptor inhibitor, and the EGF, and the culture step D includes a culturing (d-2), which is performed after the culturing (d-1), in a presence of the MEK1 inhibitor, the DNA methylation inhibitor, the TGFβ receptor inhibitor, and the EGF.

6. The method according to claim 5,
wherein a period of each of the culturing (b-3), the culturing (c-3), and the culturing (d-2) is 1 day to 10 days.

7. The method according to claim 1,
wherein the cAMP activator is Forskolin.

8. The method according to claim 1,
wherein the step (2) is performed under a condition in which cAMP is supplied to cells and/or under a condition in which a cAMP-degrading enzyme inhibitor is present.

9. The method according to claim 8,
wherein the condition in which cAMP is supplied to cells is a condition in which 8-Br-cAMP is present in a culture medium.

10. The method according to claim 8,
wherein the CAMP-degrading enzyme inhibitor is IBMX.

11. The method according to claim 1,
wherein the MEK1 inhibitor is PD98059, the DNA methylation inhibitor is 5-aza-2'-deoxycytidine, and the TGFβ receptor inhibitor is A-83-01.

12. The method according to claim 1,
wherein activin A is used as a differentiation-inducing factor in the step (1-1).

13. The method according to claim 1,
wherein FGF2 or a GSK-3β inhibitor is used as a differentiation-inducing factor in the step (1-2).

14. A method for evaluating pharmacokinetics or toxicity of a test substance using intestinal epithelial cell-like cells obtained by the method of claim 1, comprising bringing a test substance into contact with the intestinal epithelial cell-like cells obtained by the method of claim 1, and evaluating pharmacokinetics or toxicity of the test substance.

15. The method according to claim 14,
wherein the pharmacokinetics is metabolism, absorbance, excretion, drug interaction, induction of a drug metabolizing enzyme, or induction of a drug transporter.

16. A method for evaluating pharmacokinetics or toxicity of a test substance using intestinal epithelial cell-like cells obtained by the method of claim 1, comprising the following steps (i) to (iii):
the step (i) of preparing a cell layer formed of the intestinal epithelial cell-like cells obtained by the method of claim 1;
the step (ii) of bringing the test substance into contact with the cell layer; and
the step (iii) of quantifying the test substance that has permeated the cell layer and evaluating absorbability or membrane permeability, drug interaction, induction of a drug metabolizing enzyme, induction of a drug transporter, or toxicity of the test substance.

* * * * *